(12) United States Patent
Hashimoto et al.

(10) Patent No.: US 9,397,298 B2
(45) Date of Patent: Jul. 19, 2016

(54) ORGANIC COMPOUND, ORGANIC LIGHT-EMITTING DEVICE, AND IMAGE DISPLAY DEVICE

(75) Inventors: Masashi Hashimoto, Tokyo (JP); Jun Kamatani, Tokyo (JP); Takayuki Horiuchi, Tokyo (JP); Hirokazu Miyashita, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 458 days.

(21) Appl. No.: 13/978,058

(22) PCT Filed: Dec. 9, 2011

(86) PCT No.: PCT/JP2011/079261
§ 371 (c)(1),
(2), (4) Date: Jul. 2, 2013

(87) PCT Pub. No.: WO2012/093578
PCT Pub. Date: Jul. 12, 2012

(65) Prior Publication Data
US 2013/0292662 A1 Nov. 7, 2013

(30) Foreign Application Priority Data

Jan. 7, 2011 (JP) .................................. 2011-002263

(51) Int. Cl.
| | |
|---|---|
| *H01L 51/50* | (2006.01) |
| *H01L 51/00* | (2006.01) |
| *C07C 13/62* | (2006.01) |
| *C07C 211/61* | (2006.01) |

(Continued)

(52) U.S. Cl.
CPC ............ *H01L 51/0058* (2013.01); *C07C 13/62* (2013.01); *C07C 211/61* (2013.01); *C09K 11/06* (2013.01); *H01L 51/006* (2013.01); *H01L 51/0056* (2013.01); *H01L 51/0067* (2013.01); *H01L 51/0074* (2013.01); *H05B 33/14* (2013.01); *C07C 2103/54* (2013.01); *C09K 2211/1011* (2013.01); *H01L 51/0072* (2013.01); *H01L 51/5012* (2013.01); *H01L 2251/5384* (2013.01)

(58) Field of Classification Search
CPC .. C07C 13/62; C07C 2103/54; C07C 211/61; C09K 11/06; C09K 2211/1011; H01L 2251/5384; H01L 51/0056; H01L 51/0058; H01L 51/006; H01L 51/0067; H01L 51/0072; H01L 51/0074; H01L 51/5012; H05B 33/14
See application file for complete search history.

(56) References Cited

U.S. PATENT DOCUMENTS

| | | | | |
|---|---|---|---|---|
| 6,803,120 | B2 * | 10/2004 | Fukuoka ................ | C09K 11/06 313/504 |
| 6,866,947 | B1 * | 3/2005 | Fukuoka ................ | C09K 11/06 313/504 |

(Continued)

FOREIGN PATENT DOCUMENTS

| | | |
|---|---|---|
| JP | 10-330295 A | 12/1998 |
| JP | 11-40360 A | 2/1999 |

(Continued)

*Primary Examiner* — Dawn Garrett
(74) *Attorney, Agent, or Firm* — Canon U.S.A., Inc., IP Division

(57) ABSTRACT

The present invention provides an organic compound having a basic skeleton which has an emission wavelength in the yellow region, a high luminous efficiency, and good sublimability.

12 Claims, 1 Drawing Sheet

(51) Int. Cl.
    *C09K 11/06*    (2006.01)
    *H05B 33/14*    (2006.01)

(56) References Cited

U.S. PATENT DOCUMENTS

| 8,963,813 B2* | 2/2015 | Kamatani | H01L 51/0056 |
| | | | 345/76 |
| 2004/0076853 A1* | 4/2004 | Jarikov | C09K 11/06 |
| | | | 428/690 |

FOREIGN PATENT DOCUMENTS

| JP | 2002-164176 | * | 6/2002 |
| JP | 2003-347057 A | | 12/2003 |
| JP | 2005-68087 A | | 3/2005 |
| JP | 2008-187185 A | | 8/2008 |
| JP | 2009-1499 A | | 1/2009 |
| JP | 2009-302470 A | | 12/2009 |
| JP | 2011-501462 A | | 1/2011 |

* cited by examiner

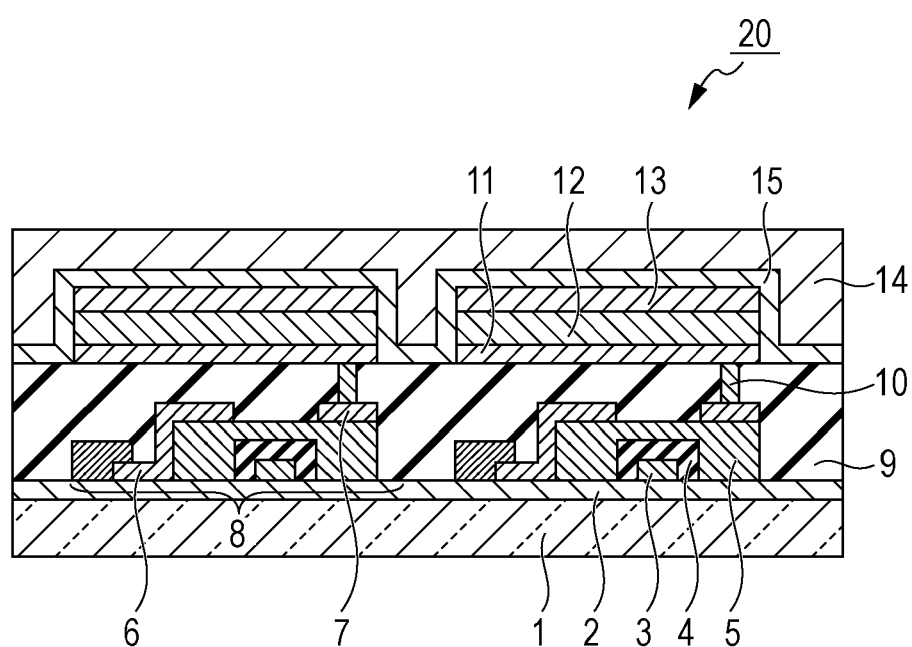

ORGANIC COMPOUND, ORGANIC LIGHT-EMITTING DEVICE, AND IMAGE DISPLAY DEVICE

TECHNICAL FIELD

The present invention relates to an organic compound, and an organic light-emitting device and an image display device using the organic compound.

BACKGROUND ART

Organic light-emitting devices (organic EL devices) are electronic elements each including a pair of electrodes and an organic compound layer disposed between the electrodes. Electrons and holes are injected from the pair of electrodes to generate excitons of a light-emitting organic compound in the organic compound layer, so that the organic light-emitting devices emit light when the excitons are returned to the ground state.

Organic light-emitting devices have been recently significantly developed, and characteristics thereof include low drive voltages, a variety of emission wavelengths, high-speed response, and the possibility of reduction in thickness and weight of light-emitting devices.

In addition, light-emitting organic compounds have been actively created so far. This is because the creation of compounds having excellent light emission properties is important for providing high-performance organic light-emitting devices.

Examples of compounds that have been created so far include compound 1-A described below and proposed in PTL 1. The compound has fluoroantheno[8,9-k]fluoranthene as a basic skeleton. Light emitted from the skeleton is blue light.

[Chem. 1]

1-A

PTL 2 proposes compound 1-B below, and PTL 3 proposes compound 1-C below. The compound 1-B below is disclosed as a material for organic TFT (Thin Film Transistor).

[Chem. 2]

1-B

-continued

1-C

CITATION LIST

Patent Literature

PTL 1 Japanese Patent Laid-Open No. 11-40360
PTL 2 Japanese Patent Laid-Open No. 2009-302470
PTL 3 Japanese Patent Laid-Open No. 10-330295

However, the compound 1-C has high emission intensity but has large intermolecular interaction because of its high molecular planarity and symmetry. Therefore, the compound 1-C has low sublimability.

However, it is known that even when materials in organic light-emitting devices have the same luminescence quantum yield, the luminance depends on wavelengths. This is because luminosity factor depends on emission wavelengths. In this case, the luminosity factor is maximized at a wavelength of 555 nm.

Therefore, in order to achieve an organic light-emitting device with high efficiency, a material having a peak emission wavelength near 555 nm (yellow region) is required. However, the development of such a material has not yet been satisfactory.

In addition, compounds having the basic skeletons proposed in PTLs 1 to 3 include no compound having an emission in the yellow region and good luminous efficiency and sublimability.

SUMMARY OF INVENTION

The present invention provides an organic compound having a basic skeleton having an emission wavelength within the yellow region, a high luminous efficiency, and good sublimability.

An organic compound according to the present invention is a compound represented by the following general formula (1).

[Chem. 3]

(1)

In the formula (1), $R_1$ to $R_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

According to the present invention, it is possible to provide an organic compound having a basic skeleton having an emission wavelength within the yellow region, a high luminous efficiency, and good sublimability.

BRIEF DESCRIPTION OF DRAWINGS

FIG. 1 is a schematic sectional view showing an example of a display device including an organic light-emitting device according to an embodiment of the present invention and a TFT electrically connected to the organic light-emitting device.

DESCRIPTION OF EMBODIMENTS

An organic compound according to the present invention is an organic compound represented by the following general formula (1).

[Chem. 4]

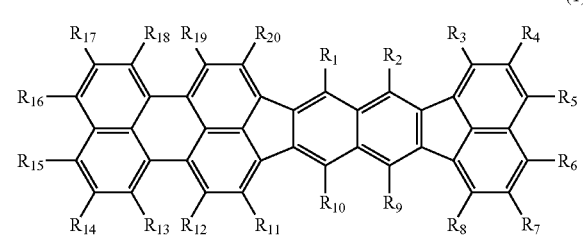

(1)

In the formula (1), $R_1$ to $R_{20}$ are each independently a hydrogen atom or a substituent selected from a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, and a substituted or unsubstituted aryloxy group.

In the organic compound according to the present invention, preferably, $R_1$ to $R_{20}$ in the formula (1) are each independently a hydrogen atom or a substituent selected from substituted or unsubstituted alkyl groups.

Examples of a halogen atom represented by $R_1$ to $R_{20}$ include, but of course not limited to, fluorine, chlorine, bromine, iodine, and the like.

Examples of an alkyl group represented by $R_1$ to $R_{20}$ include, but of course not limited to, a methyl group, an ethyl group, a normal propyl group, an isopropyl group, a normal butyl group, a tertiary butyl group, a secondary butyl group, an octyl group, a 1-adamantyl group, 2-adamantyl group, and the like.

Among these, a tertiary butyl group having a large excluded volume is preferred from the viewpoint of sublimability, and the molecular structure more preferably has two or more tertiary butyl groups. However, this represents that the molecular structure preferably contains two or more tertiary butyl groups including those introduced in substituents represented by $R_1$ to $R_{20}$, but not represent that two or more of $R_1$ to $R_{20}$ are tertiary butyl groups.

Examples of an alkoxy group represented by $R_1$ to $R_{20}$ include, but of course not limited to, a methoxy group, an ethoxy group, a propoxy group, a 2-ethyl-octyloxy group, a benzyloxy group, and the like.

Examples of an amino group represented by $R_1$ to $R_{20}$ include, but of course not limited to, a N-methylamino group, a N-ethylamino group, a N,N-dimethylamino group, a N,N-diethylamino group, a N-methyl-N-ethylamino group, a N-benzylamino group, a N-methyl-N-benzylamino group, a N,N-dibenzylamino group, an anilino group, a N,N-diphenylamino group, a N,N-dinaphthylamino group, a N,N-difluorenylamino group, a N-phenyl-N-tolylamino group, a N,N-ditolylamino group, a N-methyl-N-phenylamino group, a N,N-dianisolylamino group, a N-mesityl-N-phenylamino group, a N,N-dimesitylamino group, a N-phenyl-N-(4-tertiary butylphenyl)amino group, a N-phenyl-N-(4-trifluoromethylphenyl)amino group, and the like.

Examples of an aryl group represented by $R_1$ to $R_{20}$ include, but of course not limited to, a phenyl group, a naphthyl group, an indenyl group, a biphenyl group, a terphenyl group, a fluorenyl group, and the like.

Examples of a heterocyclic group represented by $R_1$ to $R_{20}$ include, but of course not limited to, a pyridyl group, a pyrimidyl group, a pyrazyl group, an oxazolyl group, an oxadiazolyl group, a thiazolyl group, a thiadiazolyl group, a carbazolyl group, an acridinyl group, a phenanthrolyl group, a dibenzothiophenyl group, and the like.

Examples of an aryloxy group represented by $R_1$ to $R_{20}$ include, but of course not limited to, a phenoxy group, a 4-tert-butylphenoxy group, a thienyloxy group, and the like.

Examples of a substituent contained in each of the alkyl group, the alkoxy group, the amino group, the aryl group, the heterocyclic group, and the aryloxy group include, but of course not limited to, alkyl groups such as a methyl group, an ethyl group, an isopropyl group, a tert-butyl group, and the like; aralkyl groups such as a benzyl group and the like; aryl groups such as a phenyl group, a biphenyl group, and the like; heterocyclic groups such as a pyridyl group, a pyrrolyl group, and the like; amino groups such as a dimethylamino group, a diethylamino group, a dibenzylamino group, a diphenylamino group, a ditolylamino group, and the like; alkoxy groups such as a methoxy group, an ethoxy group, a propoxy group, and the like; aryloxy groups such as a phenoxy group and the like; halogen atoms such as fluorine, chlorine, bromine, iodine, and the like; and a cyano group.

Next, a method for synthesizing the organic compound according to the present invention is described. The organic compound according to the present invention is synthesized, for example, according to a synthesis scheme shown below.

Synthesis route 1

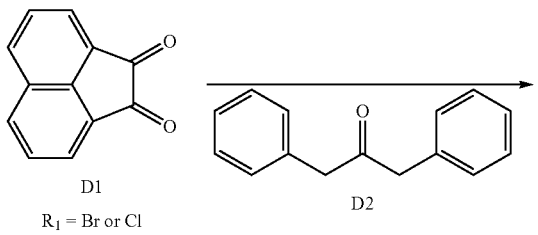

[Chem. 5]

$R_1$ = Br or Cl

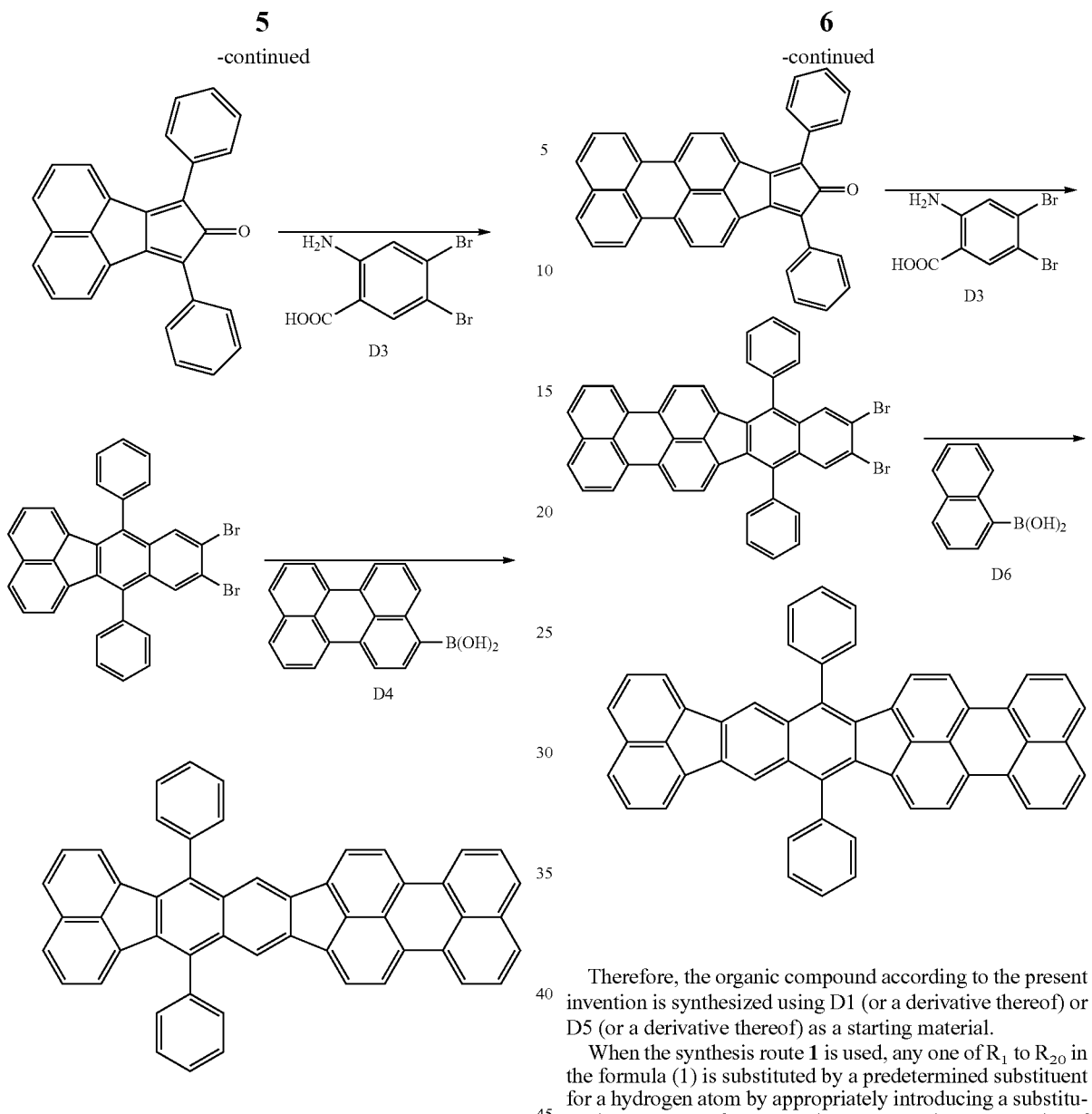

Therefore, the organic compound according to the present invention is synthesized using D1 (or a derivative thereof) or D5 (or a derivative thereof) as a starting material.

When the synthesis route 1 is used, any one of $R_1$ to $R_{20}$ in the formula (1) is substituted by a predetermined substituent for a hydrogen atom by appropriately introducing a substituent into any one of compounds D1, D2, and D4. Examples of the substituent introduced include an alkyl group, a halogen atom, a phenyl group, and the like. When the synthesis route 2 is used, a hydrogen atom of any one of $R_1$ to $R_{20}$ in the formula (1) is substituted by a predetermined substituent by appropriately introducing a substituent into any one of compounds D2, D5, and D6.

In the above-described synthesis scheme, various organic compounds can be synthesized by changing D1 to D6. Examples of the organic compounds, together with the raw materials D1 to D6, are shown in Table 1 below.

TABLE 1-continued
| | | | | |
|---|---|---|---|---|
| 2 | 1 | 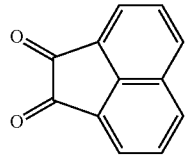 [SMILES: O=C1C(=O)c2cccc3cccc1c23] | 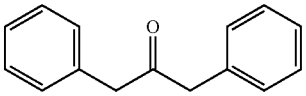 [SMILES: O=C(Cc1ccccc1)Cc1ccccc1] | 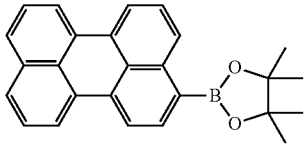 [SMILES: CC1(C)OB(c2ccc3c4cccc5cccc(c6cccc2c63)c54)OC1(C)C] |
| 3 | 1 | 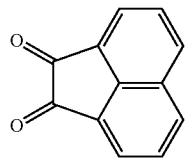 [SMILES: O=C1C(=O)c2cccc3cccc1c23] | 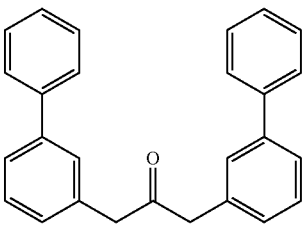 [SMILES: O=C(Cc1cccc(-c2ccccc2)c1)Cc1cccc(-c2ccccc2)c1] | 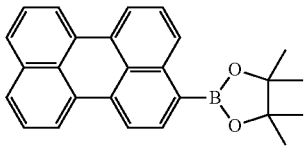 |
| 4 | 1 | 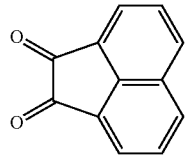 [SMILES: O=C1C(=O)c2cccc3cccc1c23] | 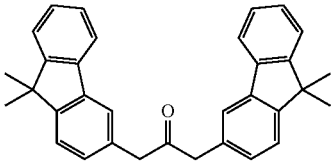 | 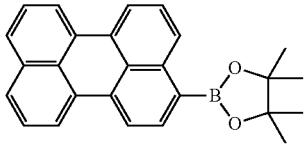 [SMILES: CC1(C)OB(c2ccc3c4cccc5cccc(c6cccc2c63)c54)OC1(C)C] |
| 5 | 1 | 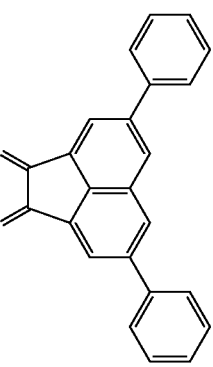 | 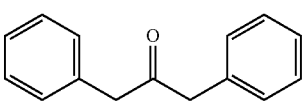 [SMILES: O=C(Cc1ccccc1)Cc1ccccc1] | 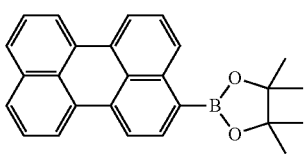 [SMILES: CC1(C)OB(c2ccc3c4cccc5cccc(c6cccc2c63)c54)OC1(C)C] |
| 6 | 2 | 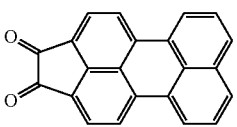 [SMILES: O=C1C(=O)c2ccc3c4cccc5cccc(c6ccc1c2c63)c54] | 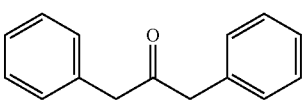 [SMILES: O=C(Cc1ccccc1)Cc1ccccc1] | 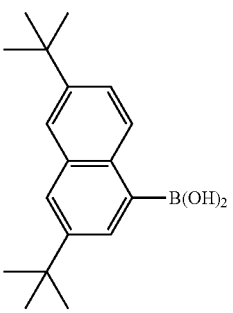 [SMILES: CC(C)(C)c1ccc2c(B(O)O)cc(C(C)(C)C)cc2c1] |
| 7 | 1 | 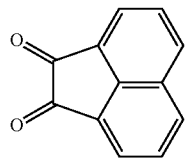 | 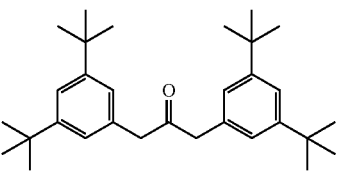 [SMILES: CC(C)(C)c1cc(CC(=O)Cc2cc(C(C)(C)C)cc(C(C)(C)C)c2)cc(C(C)(C)C)c1] | 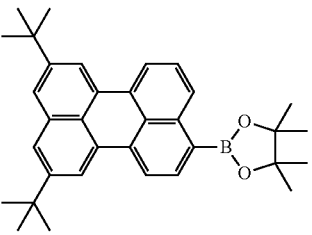 [SMILES: CC(C)(C)c1cc2cc(C(C)(C)C)cc3c4ccc(B5OC(C)(C)C(C)(C)O5)c5cccc(c(c1)c23)c54] |

TABLE 1-continued

| | | | | |
|---|---|---|---|---|
| 8 | 1 | (structure) | (structure) | (structure) |
| 9 | 2 | (structure) | (structure) | (structure) |

| Synthesis example | Synthetic compound | Exemplified compound |
|---|---|---|
| 1 | (structure) | XX-1 |
| 2 | (structure) | XX-2 |
| 3 | (structure) | XX-5 |

TABLE 1-continued
| | | |
|---|---|---|
| 4 | 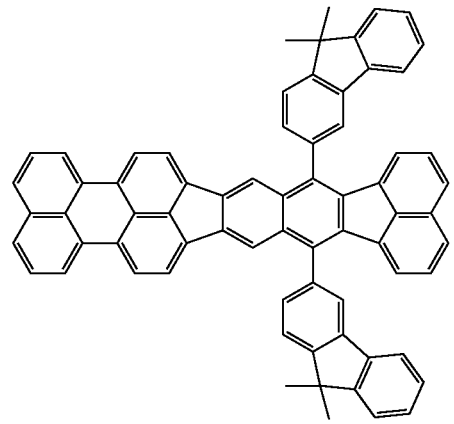 [SMILES: CC1(C)c2ccccc2-c2cc(-c3c4cc5c(cc4c(-c4ccc6c(c4)-c4ccccc4C6(C)C)c4c6cccc7cccc(c34)c76)c3ccc4c6cccc7cccc(c8ccc5c3c84)c76)ccc21] | XX-7 |
| 5 | 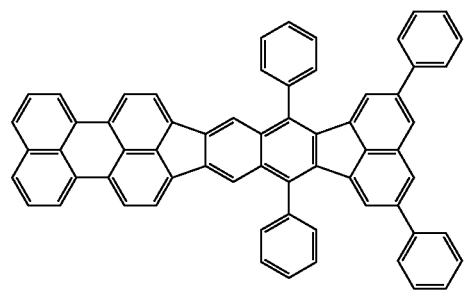 [SMILES: c1ccc(-c2cc3cc(-c4ccccc4)cc4c5c(-c6ccccc6)c6cc7c(cc6c(-c6ccccc6)c5c(c2)c34)c2ccc3c4cccc5cccc(c6ccc7c2c36)c54)cc1] | XX-10 |
| 6 | 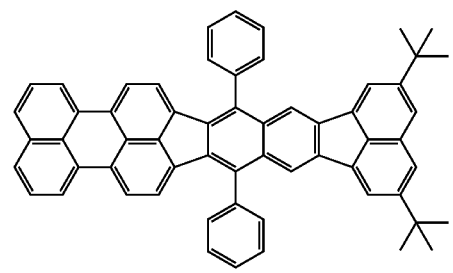 [SMILES: CC(C)(C)c1cc2cc(C(C)(C)C)cc3c4cc5c(-c6ccccc6)c6c7ccc8c9cccc%10cccc(c%11ccc(c6c(-c6ccccc6)c5cc4c(c1)c23)c7c%118)c%109] | XY-1 |
| 7 | 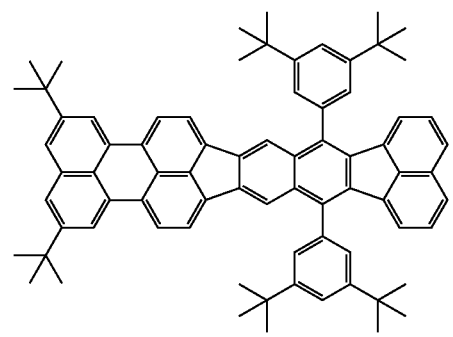 [SMILES: CC(C)(C)c1cc(-c2c3cc4c(cc3c(-c3cc(C(C)(C)C)cc(C(C)(C)C)c3)c3c5cccc6cccc(c23)c65)c2ccc3c5cc(C(C)(C)C)cc6cc(C(C)(C)C)cc(c7ccc4c2c73)c65)cc(C(C)(C)C)c1] | XY-3 |

TABLE 1-continued

8 XY-5

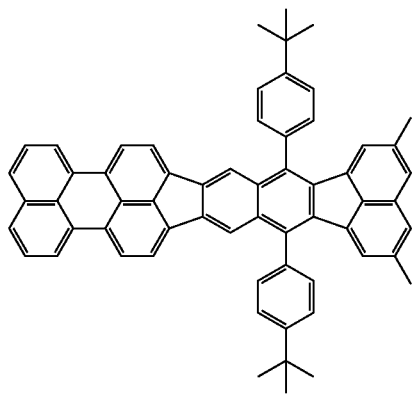 [SMILES: Cc1cc2cc(C)cc3c4c(-c5ccc(C(C)(C)C)cc5)c5cc6c(cc5c(-c5ccc(C(C)(C)C)cc5)c4c(c1)c23)c1ccc2c3cccc4cccc(c5ccc6c1c25)c43]

9 XY-6

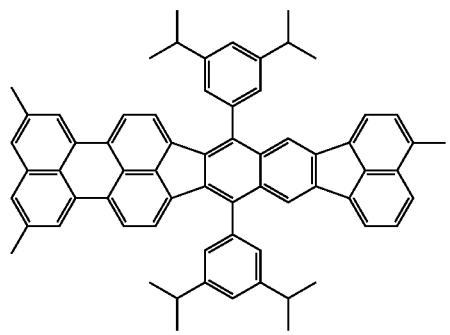 [SMILES: Cc1cc2cc(C)cc3c4ccc5c6c(-c7cc(C(C)C)cc(C(C)C)c7)c7cc8c(cc7c(-c7cc(C(C)C)cc(C(C)C)c7)c6c6ccc(c(c1)c23)c4c65)c1cccc2c(C)ccc8c21]

In order to develop the organic compound represented by the formula (1), the inventors paid attention to the basic skeleton thereof. Specifically, the inventors attempted to provide an organic compound in which only the basic skeleton molecule has an emission wavelength within a desired emission wavelength region.

A known method for achieving a desired emission wavelength includes controlling the emission wavelength of the compound by providing a specified substituent to the basic skeleton. However, this method may impair the stability of the compound.

In an embodiment of the present invention, the desired emission wavelength region is the yellow region, and specifically 530 nm or more and 580 nm or less.

A compound corresponding to the basic skeleton of the organic compound according to the present invention is a compound having a peak emission wavelength in the wavelength region of 530 nm to 580 nm. Therefore, the compound is particularly preferred as a basic skeleton of an organic compound for a yellow light-emitting material.

Next, the characteristics of the organic compound according to the present invention are described by comparison with comparative compounds having structures similar to the organic compound of the present invention. Specifically, description is made by comparison with compounds represented by the following formulae (2), (3), and (4).

[Chem. 6]

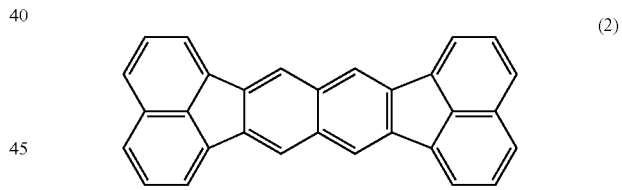

(2)

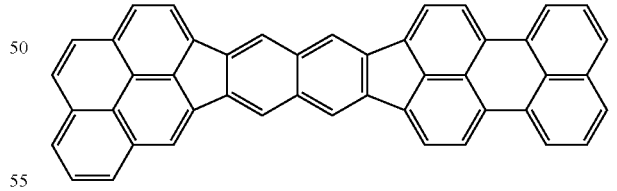

(3)

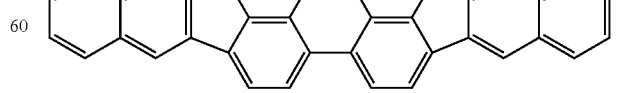

(4)

The organic compound according to the present invention is a compound having a basic skeleton represented by the following formula (5).

[Chem. 7]

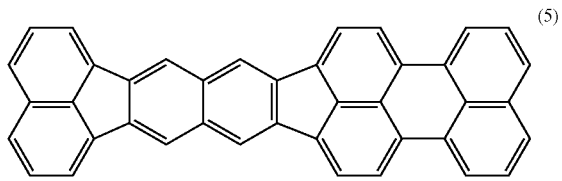

(5)

Here, the inventors made a comparison of physical properties (light emission properties and sublimability) between an organic compound represented by the formula (5) which is substituted by phenyl groups and organic compounds represented by the formulae (2), (3), and (4) each of which is substituted by phenyl groups. The results are shown in Table 2 below. In Table 2, the emission wavelength was evaluated by measurement with F4500, and the emission quantum yield was measured with an absolute quantum yield system (manufactured by Hamamatsu Photonics Co., Ltd.). Further the sublimability was evaluated by heating a sample under the condition of a degree of vacuum of about $5.0 \times 10^{-4}$ Pa.

TABLE 2

| Compound | Structural formula | Emission wavelength | Quantum yield | Sublimability |
|---|---|---|---|---|
| (1) | | 458 | 0.76 | o |
| (2) | | 550 | 0.68 | Δ |
| (3) | | 597 | 0.60 | x |

TABLE 2-continued

| Compound | Structural formula | Emission wavelength | Quantum yield | Sublimability |
|---|---|---|---|---|
| (4) | 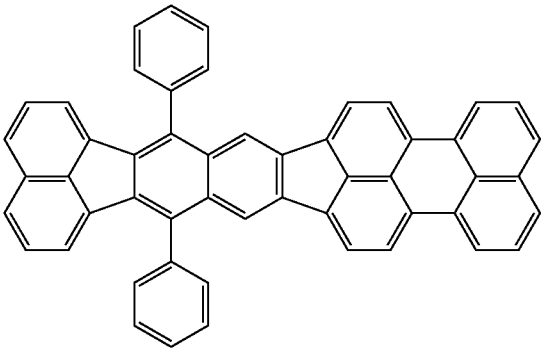 [SMILES: c1ccc(-c2c3cc4c(cc3c(-c3ccccc3)c3c5cccc6cccc(c23)c65)c2ccc3c5cccc6cccc(c7ccc4c2c73)c65)cc1] | 550 | 0.78 | ○ |

In Table 2, compound (1) is a compound in which a perylene ring moiety contained in the basis skeleton of the organic compound according to the present invention is replaced by a naphthalene ring. Table 2 indicates that the compound (1) is a compound which emits blue light because of its emission wavelength (458 nm). However, the emission is significantly different from the light emission characteristic (yellow light emission) required in the present invention.

In Table 2, compound (2) is a compound in which one of a plurality of naphthalene ring moieties contained in the basic skeleton of the organic compound according to the present invention is replaced by a pyrene ring. In Table 2, the compound (2) has a basic skeleton completely different from that of the organic compound according to the present invention but emits light within substantially the same emission region. In addition, the compound (2) shows a luminescent quantum yield that is slightly lower than but substantially the same as the organic compound according to the present invention. However, the sublimability of the compound (2) is clearly different from the organic compound according to the present invention. That is, the sublimability is clearly lower than that of the organic compound according to the present invention. This is due to the phenomenon that the molecular weight is increased by replacing the naphthalene ring moiety with the pyrene ring. Also, this is due to the phenomenon that the molecular n-electron plane is increased to enhance intermolecular interaction as compared with the organic compound according to the present invention.

In Table 2, compound (3) is considered to be an isomer of the organic compound according to the present invention in view of the basic skeleton that contains two naphthalene rings and one perylene ring. Table 2 indicates that the compound (3) is a compound showing red light emission because of its emission wavelength (597 nm). However, the emission is significantly different from the light emission characteristic (yellow light emission) required in the present invention. In addition, it is found that the compound (3) sublimates in association with decomposition. Sublimation of a compound in association with decomposition causes a decrease in drive life of a light-emitting element. Therefore, the compound (3) is undesirable as a material for a light-emitting element.

Therefore, only the organic compound according to the present invention has a skeleton that has a high quantum yield and sublimability while maintaining the desired emission wavelength.

Also, a compound corresponding the basic skeleton of the organic compound according to the present invention is a molecule with high planarity. Therefore, in the form of a thin film, molecular overlap (stacking) is highly likely to occur. Consequently, as well as molecular emission (monomer emission), emission (excimer emission) in a wavelength region extremely longer than the molecular emission undesirably occurs. In order to avoid this, a substituent is introduced into the basic skeleton represented by the formula (1). In particular, in order to prevent the stacking, it is effective to introduce an aryl group into any one of $R_1$, $R_2$, $R_9$, and $R_{20}$ in the formula (1) because the plane of the aryl group introduced is positioned more perpendicularly to the plane of the basic skeleton.

Since the organic compound according to the present invention has two five-membered rings in its skeleton, the compound has a low HOMO (Highest Occupied Molecular Orbital) energy level. This represents that the compound has a low oxidation potential. Therefore, the organic compound according to the present invention is stable to oxidation.

In addition, the organic compound according to the present invention has the basic skeleton free from a heteroatom such as a nitrogen atom. This also contributes to the low oxidation potential of the compound and is a reason why the organic compound according to the present invention is stable to oxidation.

The basic skeleton of the organic compound according to the present invention has a low HOMO energy level. That is, the basic skeleton of the organic compound according to the present invention also has a low LUMO (Lowest Unoccupied Molecular Orbital) energy level.

In addition, when a substituent that shifts the emission wavelength to a longer wavelength side is introduced into the basic skeleton contained in the organic compound according to the present invention, the organic compound according to the present invention can be used as a red light-emitting material. Since the basic skeleton of a material having an emission wavelength shifted to a longer wavelength side by introducing a substituent is the same as the organic compound according to the present invention, the material is also stable to oxidation. Examples of the substituent that shifts the emission wavelength to a longer wavelength side include substituents derived from triarylamine, substituents derived from anthracene, and the like.

Examples of the compound represented by the general formula (1) are given below. However, the present invention is not limited to these examples.

[Chem. 8]
XX-1
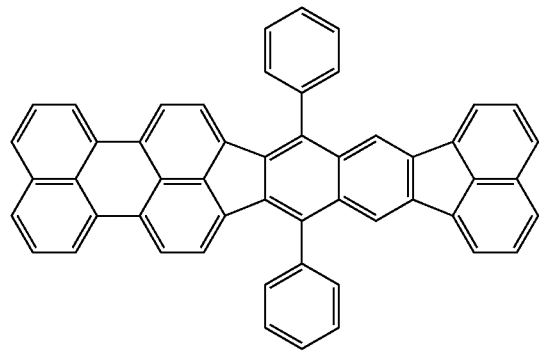
XX-2
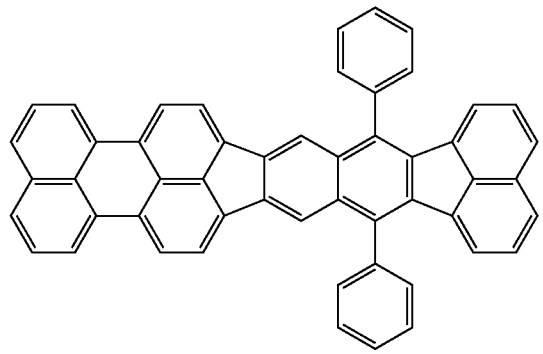
XX-3
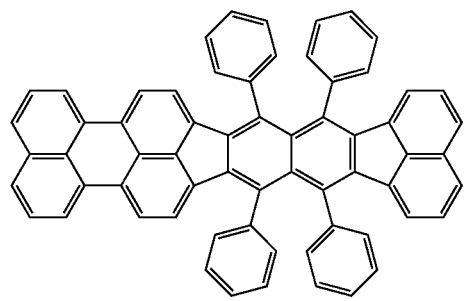
XX-4
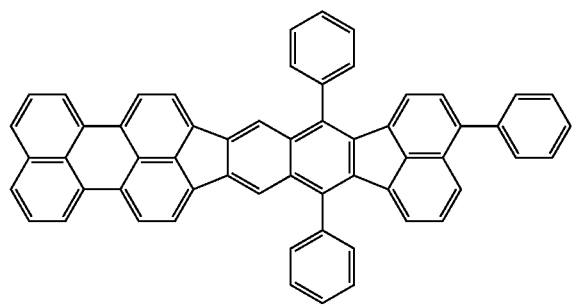
XX-5
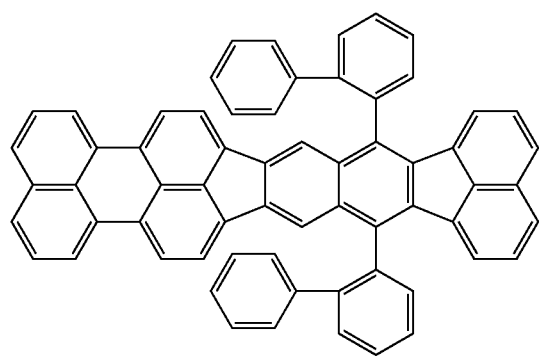
XX-6
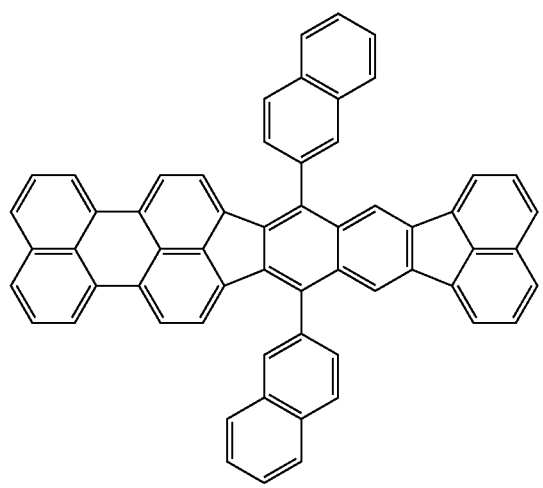

-continued
XX-7
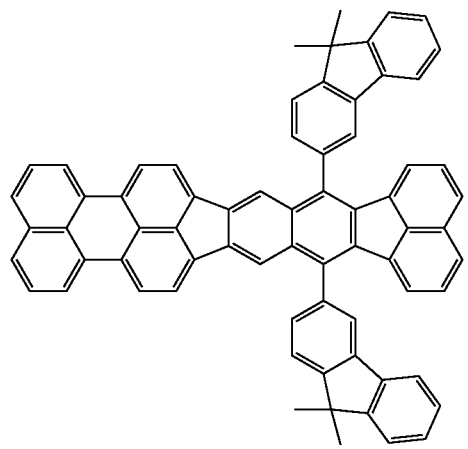
XX-8
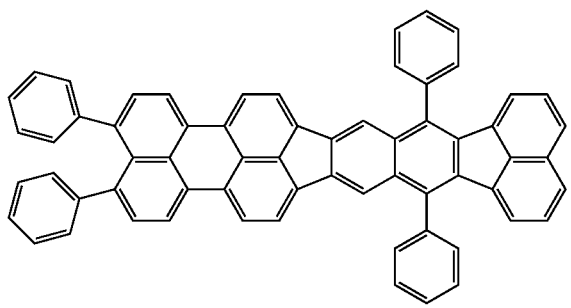
[Chem. 9]
XX-9
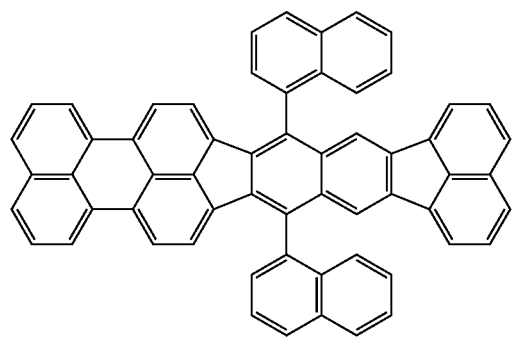
XX-10
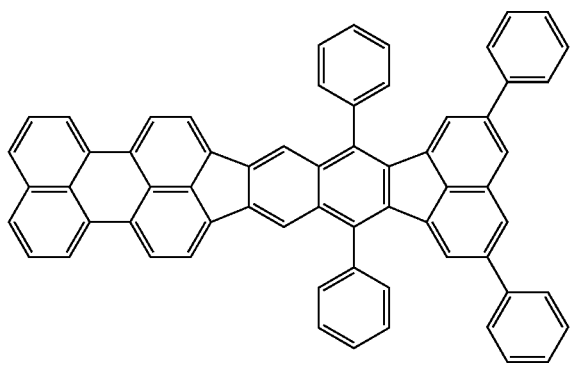
XX-11
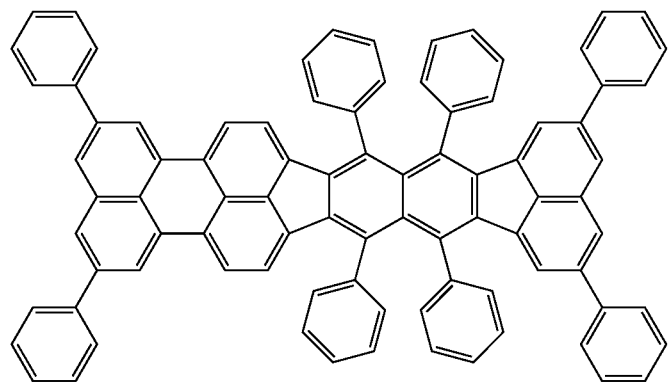
XX-12
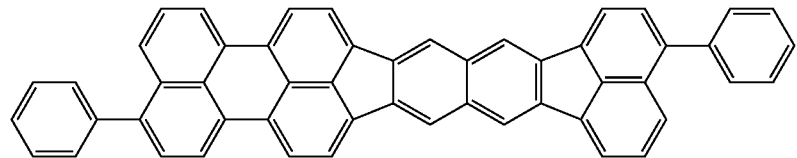

-continued
XX-13
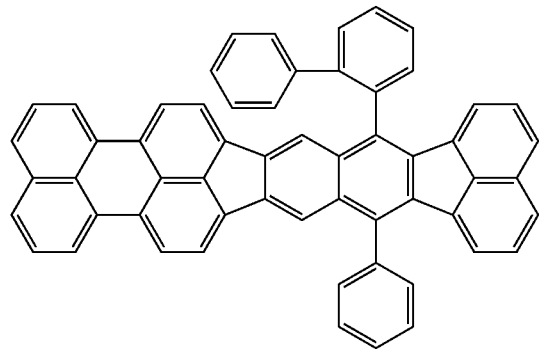
XX-14
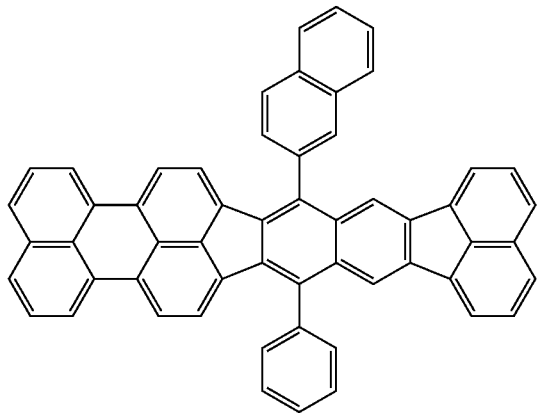
XX-15
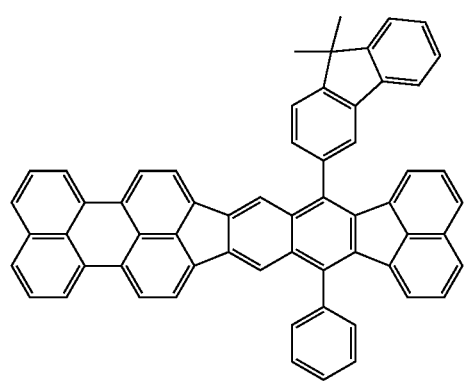
XX-16
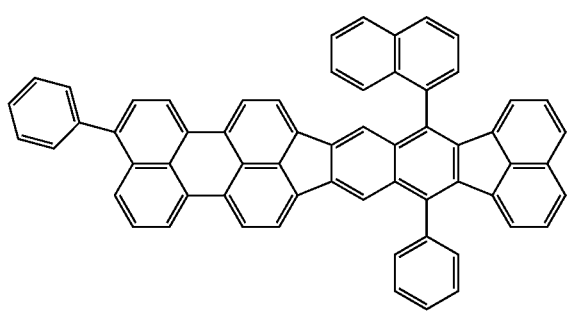
[Chem. 10]
XY-1
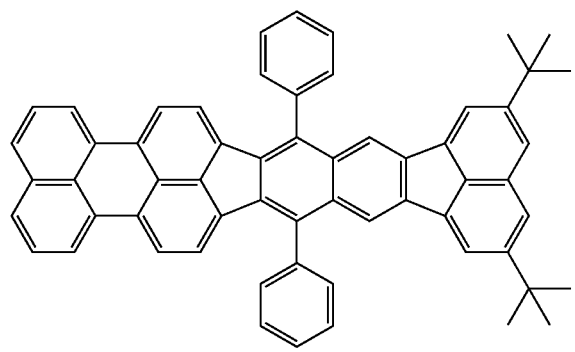
XY-2
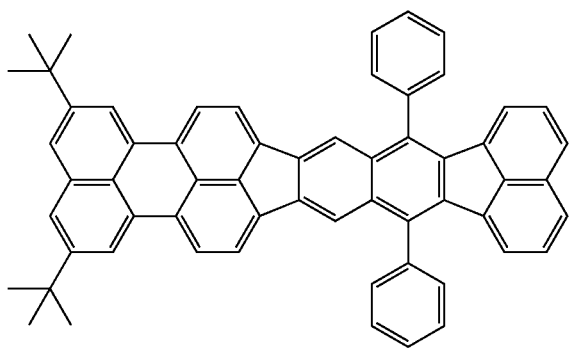
XY-3
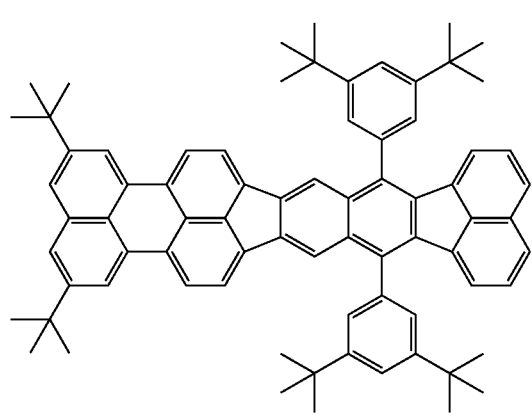
XY-4
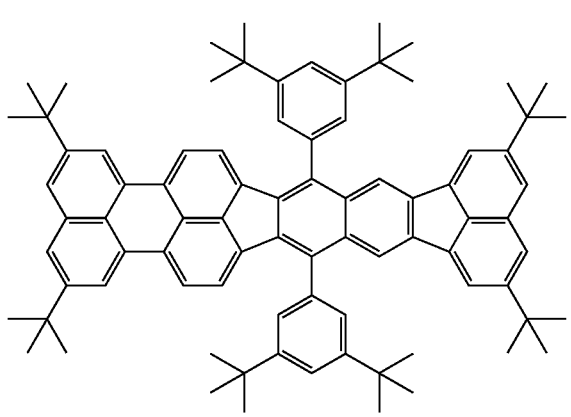

-continued
XY-5
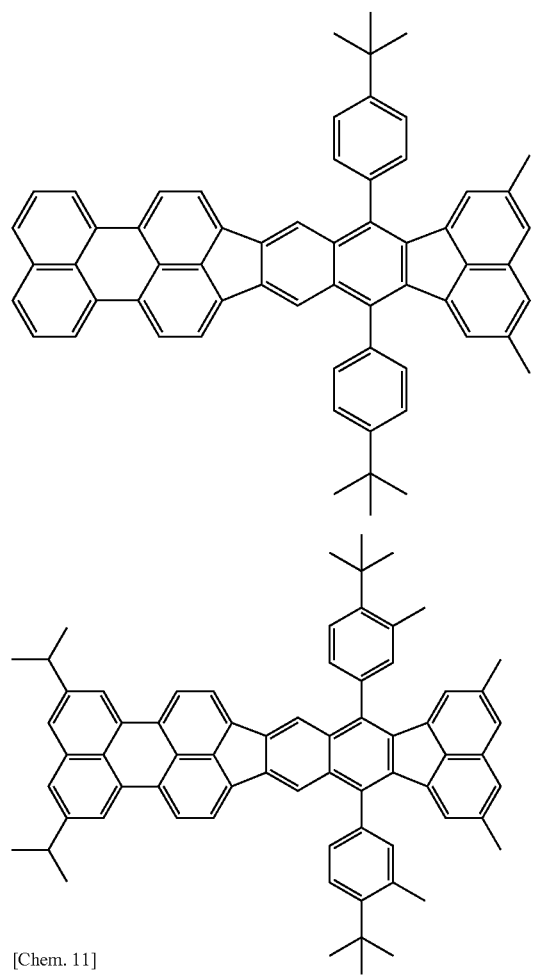
XY-6
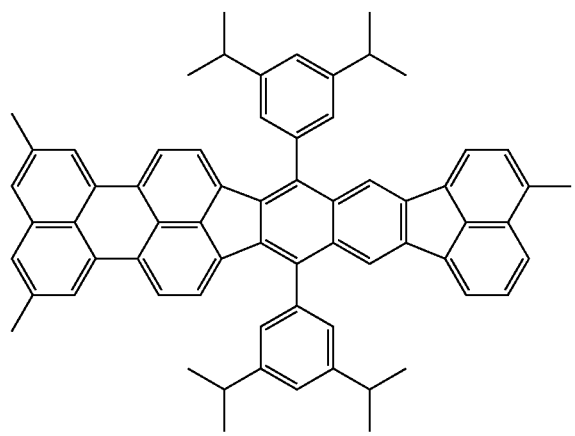
XY-7
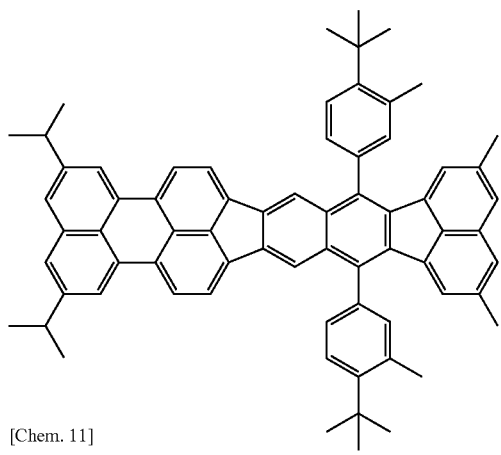
XY-8
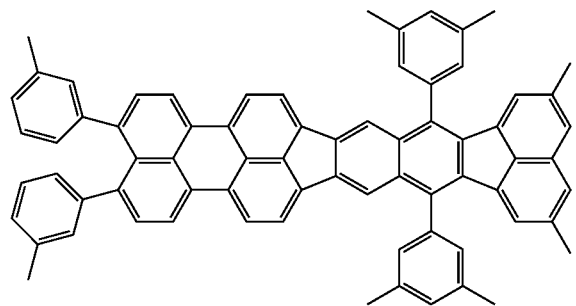
[Chem. 11]
ZZ-1
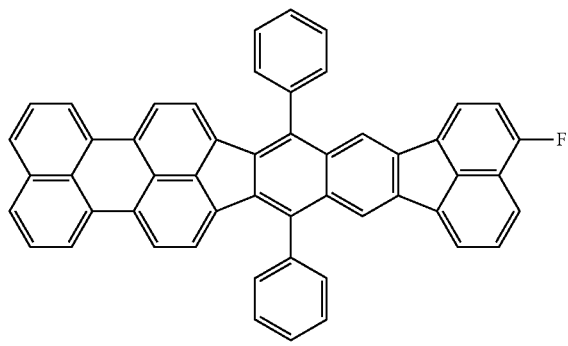
ZZ-2
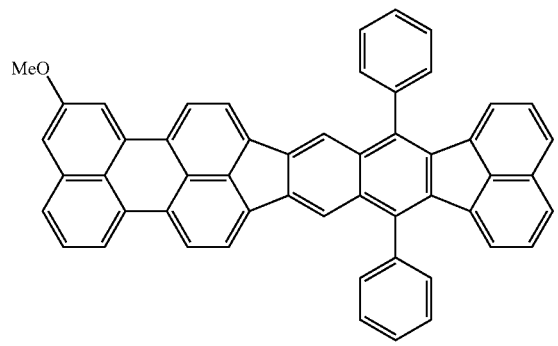
ZZ-3
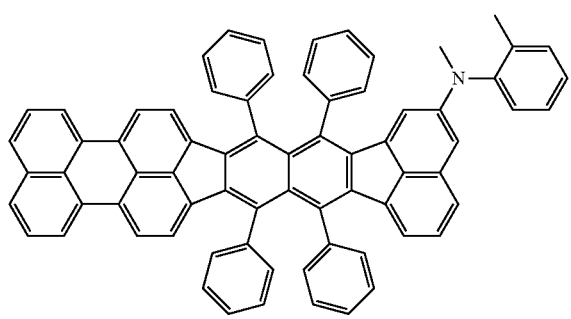
ZZ-4
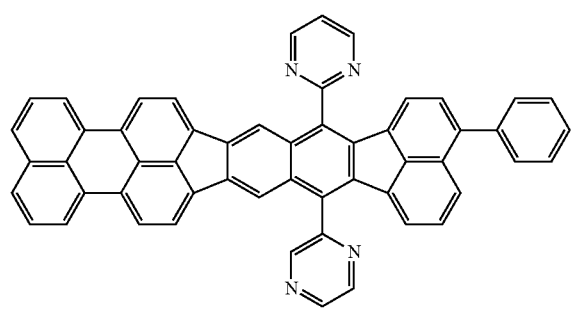

ZZ-5

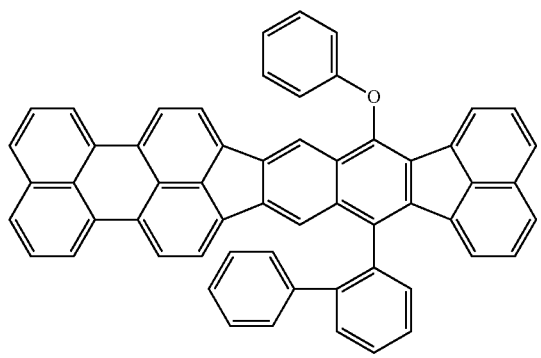

ZZ-6

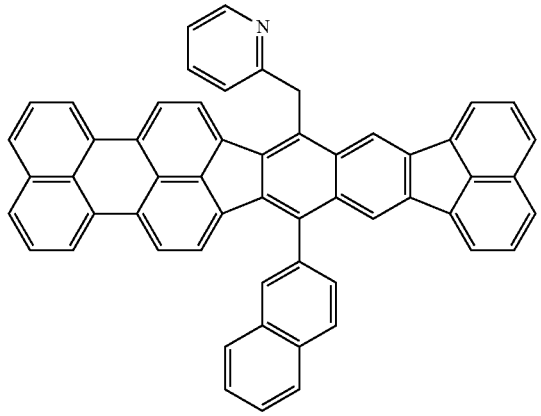

ZZ-7

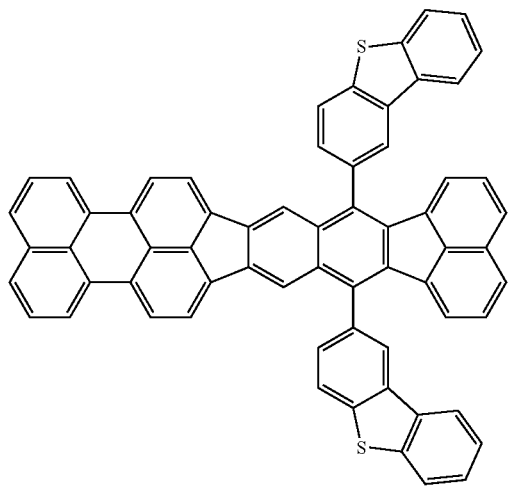

ZZ-8

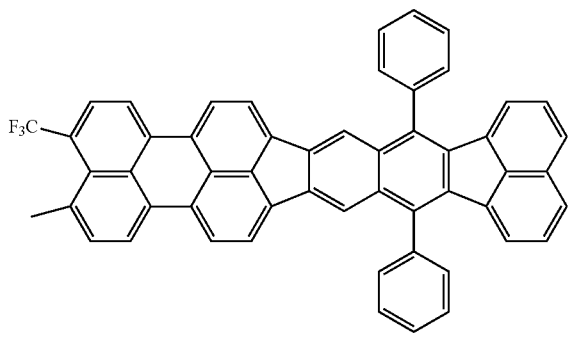

Among the above-described exemplified compounds, the compounds belonging to group XX and group XY are molecules each entirely composed of only a hydrocarbon. The compounds each composed of only a hydrocarbon generally have a low HOMO energy level. Therefore, the compounds belonging to the group XX and the group XY have a low oxidation potential, which indicates that the organic compounds are stable to oxidation.

Therefore, among organic compounds according to the present invention, organic compounds composed of only a hydrocarbon, i.e., compounds belonging to the group XX and the group XY, are desirable because of the high molecular stability.

On the other hand, among the exemplified compounds, the compounds belonging to the group ZZ each have a substituent containing a heteroatom. In this case, the oxidation potential of the molecule is significantly changed, or intermolecular interaction is changed. In addition, when a substituent contains a heteroatom, the peak emission wavelength can be shifted to a longer wavelength side. Further, the compounds in the group ZZ having a substituent containing a heteroatom are useful as electron transport, hole transport, and hole trapping light-emitting materials. Also, the organic compounds belonging to the group ZZ can be used at a high concentration of 100%.

As described above, the exemplified compounds are given as the group XX, the group XY, and the group ZZ. The organic compounds each have the basic skeleton that emits yellow light. In addition, the luminescent color of the organic compound according to the present invention can be shifted to a longer wavelength region than yellow emission, specifically red emission, by providing a proper substituent to the basic skeleton of the organic compound.

Next, an organic light-emitting device according to an embodiment of the present invention is described.

An organic light-emitting device according to an embodiment of the present invention includes at least a pair of electrodes, i.e., an anode and a cathode, and an organic compound layer disposed between the electrodes. In the organic light-emitting device of the present invention, the organic compound layer may be a single layer or a laminate including a plurality of layers as long as it has a light-emitting layer.

When the organic compound layer is a laminate including a plurality of layers, the organic compound layer may include, other than the light-emitting layer, a hole injection layer, a hole transport layer, an electron blocking layer, a hole-exciton blocking layer, an electron transport layer, an electron injection layer, and the like. In addition, the light-emitting layer may be a single layer or a laminate including a plurality of layers.

In the organic light-emitting device according to the embodiment, at least one of the organic compound layers constituting the device contains the organic compound according to the present invention. Specifically, any one of the above-described light-emitting layer, hole injection layer, hole transport layer, electron blocking layer, hole-exciton blocking layer, electron transport layer, and electron injection layer contains the organic compound according to the present invention. The light-emitting layer can contain the organic compound according to the present invention. In particular, the organic compound can be used as a guest material of a yellow light-emitting element.

In the organic light-emitting device according to the embodiment, when the light-emitting layer contains the organic compound according to the present invention, the light-emitting layer may be a layer containing only the organic compound according to the present invention or a layer containing the organic compound according to the present invention and another compound. When the light-emitting layer is a layer including the organic compound according to the present invention and another compound, the organic compound according to the present invention may be used as a host or a guest of the light-emitting layer. Alternatively, the organic compound may be used as an assist material which can be contained in the light-emitting layer.

The host is a compound having the highest weight ratio among the compounds constituting the light-emitting layer. In addition, the guest is a compound which has a lower weigh ratio than the host among the compounds constituting the light-emitting layer and which mainly contributes to light emission. The assist material is a compound which has a lower weight ratio than the host among the compounds constituting the light-emitting layer and which assists light emission of the guest. In addition, the assist material is also called a "second host".

Here, when the organic compound according to the present invention is used as the guest in the light-emitting layer, the concentration of the guest is preferably 0.01% by weight or more and 20% by weight or less, more preferably 0.2% by weight or more and 5% by weight or less, relative to the total of the light-emitting layer. In this case, the organic light-emitting device which emits yellow light by light emission of the organic compound according to the present invention can be provided using the organic compound according to the present invention as the guest of the light-emitting layer.

When the organic compound according to the present invention is used as the guest in the light-emitting layer, a material having a higher LUMO level (having a LUMO level closer to the vacuum level) than the organic compound according to the present invention can be used as the host. This is because when a material having a higher LUMO level than that of the organic compound according to the present invention is used as the host, the organic compound according to the present invention can more satisfactorily receive electrons supplied to the host in the light-emitting layer because of the lower LUMO level of the organic compound according to the present invention.

On the other hand, the organic compound according to the present invention can also be used as a host of a red light-emitting layer.

As a result of various investigations, the inventors found that when the organic compound according to the present invention is used as the host or guest of the light-emitting layer, particularly the guest of the light-emitting layer, an element having a high efficiency, high luminance, high optical output, and very high durability can be produced. This is described in detail below in examples.

On the other hand, the organic compound according to the present invention can be used as a constituent material of an organic compound layer other than the light-emitting layer constituting the organic light-emitting device of the present invention. Specifically, the organic compound may be used as a constituent material of the electron transport layer, the electron injection layer, the hole transport layer, the hole injection layer, the hole blocking layer, or the like. In this case, the luminescent color of the organic light-emitting device is not limited to red. More specifically, the luminescent color may be white or a medium color.

Besides the organic compound according to the present invention, if required, a known low-molecular or high-molecular hole injecting compound or hole transport compound, a compound serving as the host, a light-emitting compound, an electron injecting compound or electron transport compound, and the like can be used.

Examples of these compounds are given below.

As the hole injecting compound or the hole transport compound, a material having high hole mobility can be used. Examples of a low-molecular or high-molecular material having the hole injecting performance or hole transport performance include, but of course not limited to, triarylamine derivatives, phenylenediamine derivatives, stilbene derivatives, phthalocyanine derivatives, porphyrin derivatives, poly (vinylcarbazole), poly(thiophene), and other conductive polymers.

Examples of the host include compounds shown in Table 3 below.

TABLE 3

H1

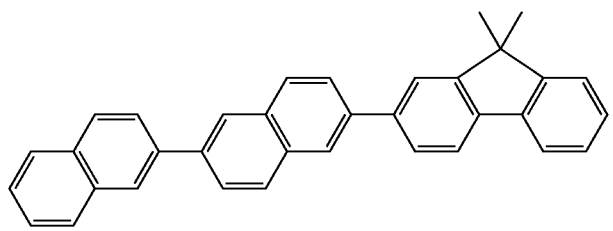 [SMILES: CC1(C)c2ccccc2-c2ccc(-c3ccc4cc(-c5ccc6ccccc6c5)ccc4c3)cc21]

TABLE 3-continued
H2
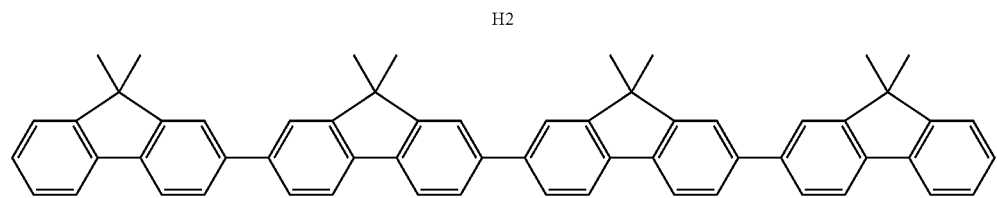
H3
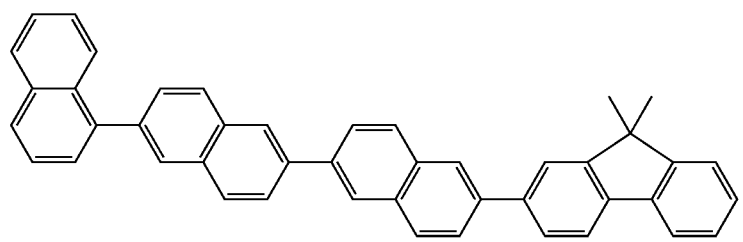 [SMILES: CC1(C)c2ccccc2-c2ccc(-c3ccc4cc(-c5ccc6cc(-c7cccc8ccccc78)ccc6c5)ccc4c3)cc21]
H4
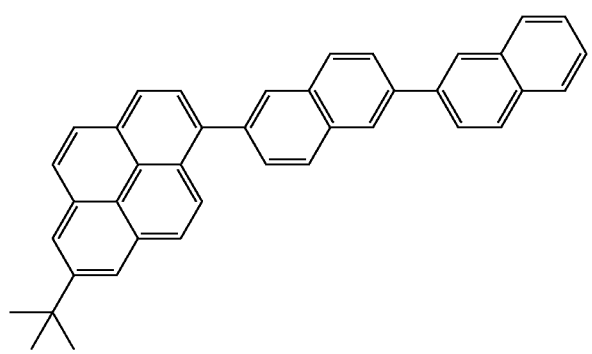 [SMILES: CC(C)(C)c1cc2ccc3ccc(-c4ccc5cc(-c6ccc7ccccc7c6)ccc5c4)c4ccc(c1)c2c34]
H5
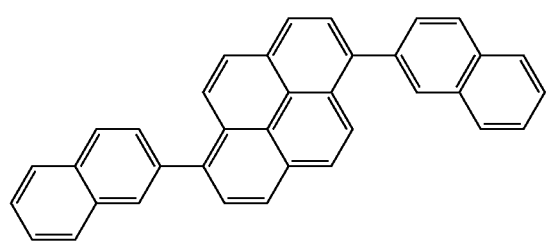 [SMILES: c1ccc2cc(-c3ccc4ccc5c(-c6ccc7ccccc7c6)ccc6ccc3c4c65)ccc2c1]
H6
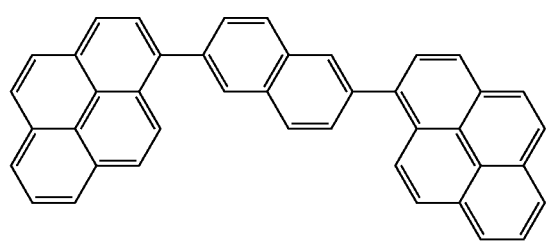 [SMILES: c1cc2ccc3ccc(-c4ccc5cc(-c6ccc7ccc8cccc9ccc6c7c89)ccc5c4)c4ccc(c1)c2c34]

TABLE 3-continued
H7
H8
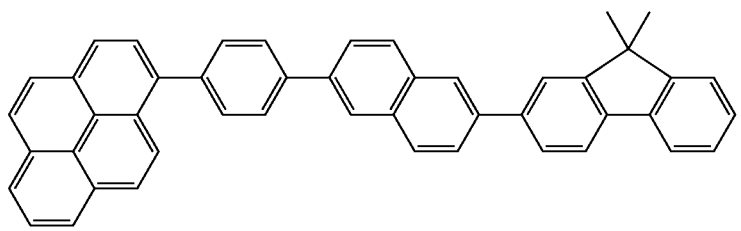 [SMILES: CC1(C)c2ccccc2-c2ccc(-c3ccc4cc(-c5ccc(-c6ccc7ccc8cccc9ccc6c7c89)cc5)ccc4c3)cc21]
H9
H10
H11

TABLE 3-continued
H12
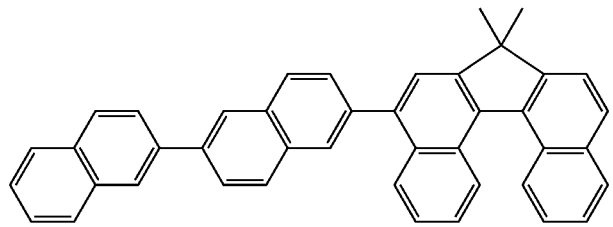 [SMILES: CC1(C)c2ccc3ccccc3c2-c2c1cc(-c1ccc3cc(-c4ccc5ccccc5c4)ccc3c1)c1ccccc21]
H13
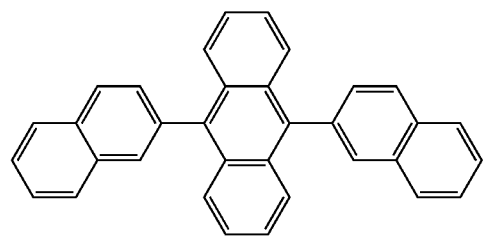 [SMILES: c1ccc2cc(-c3c4ccccc4c(-c4ccc5ccccc5c4)c4ccccc34)ccc2c1]
H14
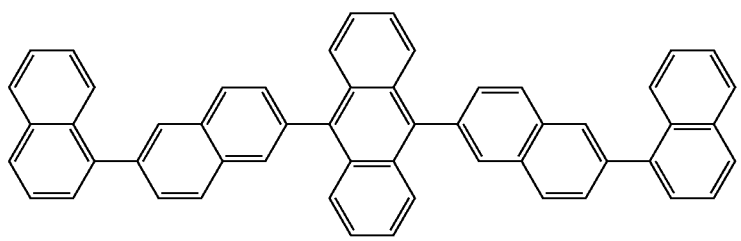 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H15
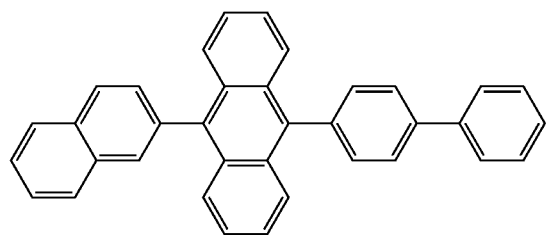 [SMILES: c1ccc(-c2ccc(-c3c4ccccc4c(-c4ccc5ccccc5c4)c4ccccc34)cc2)cc1]
H16
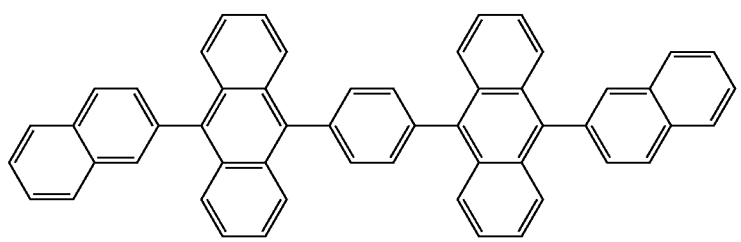 [SMILES: c1ccc2cc(-c3c4ccccc4c(-c4ccc(-c5c6ccccc6c(-c6ccc7ccccc7c6)c6ccccc56)cc4)c4ccccc34)ccc2c1]

TABLE 3-continued
H17
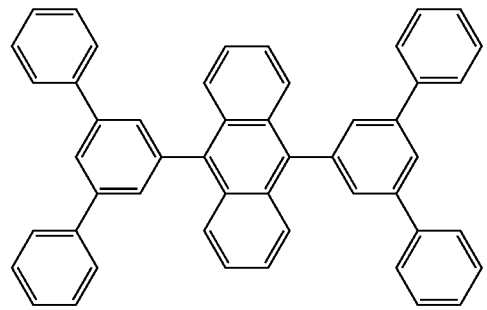 [SMILES: c1ccc(-c2cc(-c3ccccc3)cc(-c3c4ccccc4c(-c4cc(-c5ccccc5)cc(-c5ccccc5)c4)c4ccccc34)c2)cc1]
H18
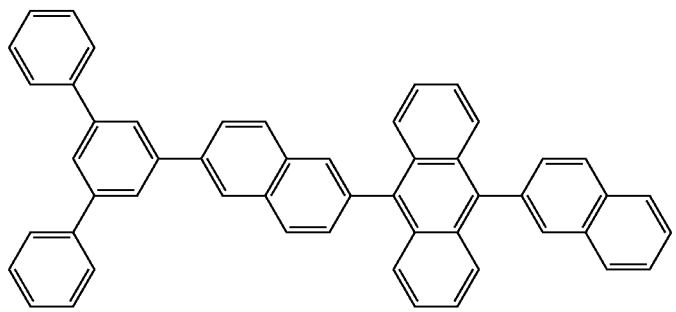 [SMILES: c1ccc(-c2cc(-c3ccccc3)cc(-c3ccc4cc(-c5c6ccccc6c(-c6ccc7ccccc7c6)c6ccccc56)ccc4c3)c2)cc1]
H19
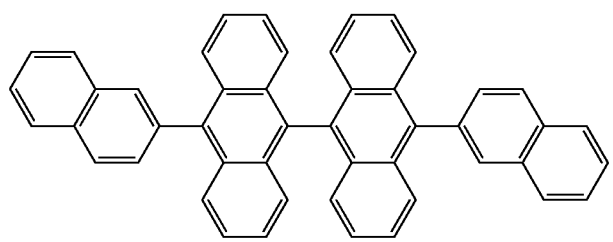 [SMILES: c1ccc2cc(-c3c4ccccc4c(-c4c5ccccc5c(-c5ccc6ccccc6c5)c5ccccc45)c4ccccc34)ccc2c1]
H20
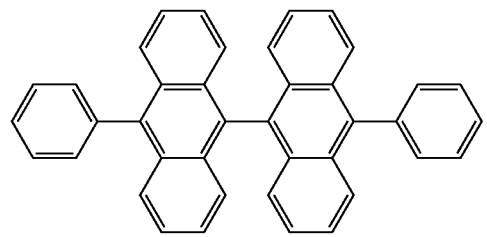 [SMILES: c1ccc(-c2c3ccccc3c(-c3c4ccccc4c(-c4ccccc4)c4ccccc34)c3ccccc23)cc1]

TABLE 3-continued

H21

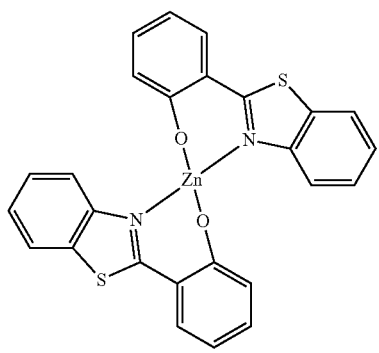

H22

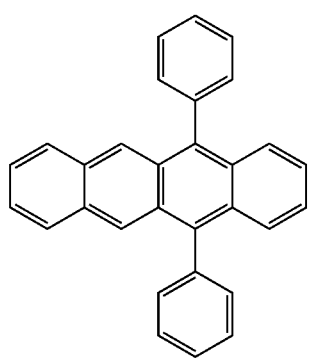 [SMILES: c1ccc(-c2c3ccccc3c(-c3ccccc3)c3cc4ccccc4cc23)cc1]

H23

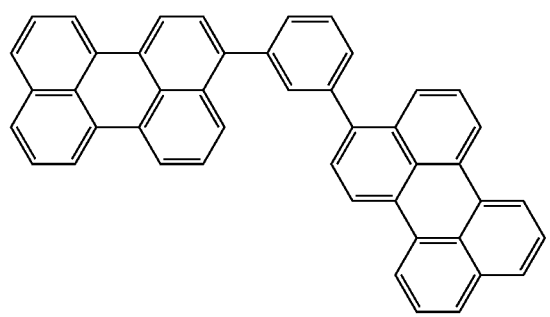 [SMILES: c1cc(-c2ccc3c4cccc5cccc(c6cccc2c63)c54)cc(-c2ccc3c4cccc5cccc(c6cccc2c63)c54)c1]

H24

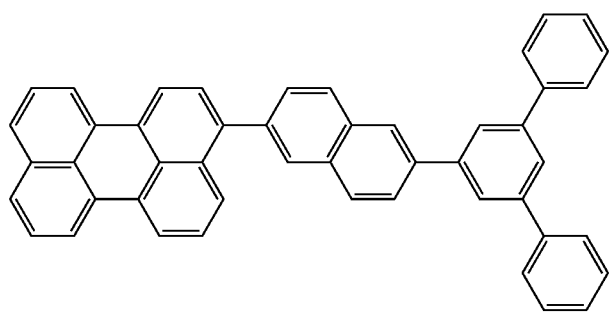 [SMILES: c1ccc(-c2cc(-c3ccccc3)cc(-c3ccc4cc(-c5ccc6c7cccc8cccc(c9cccc5c96)c87)ccc4c3)c2)cc1]

However, the present invention is not limited to these examples. Compounds which are derivatives of the compounds shown in Table 3 can also be used as the host. Other examples include, but of course not limited to, fused-ring compounds (for example, fluorene derivatives, naphthalene derivatives, anthracene derivatives, pyrene derivatives, carbazole derivatives, quinoxaline derivatives, quinoline derivatives, and the like); organic aluminum complexes such as tris(8-quinolinolate)aluminum and the like; organic zinc complexes; triphenylamine derivatives; and polymer derivatives such as poly(fluorene) derivatives, poly(phenylene) derivatives, and the like.

The electron injecting compound and the electron transport compound are appropriately selected in consideration of a balance with the hole mobility of the hole injecting compound and the hole transport compound. Examples of compounds having the electron injecting performance or electron transport performance include, but of course not limited to, oxadiazole derivatives, oxazole derivatives, pyrazine derivatives, triazole derivatives, triazine derivatives, quinoline derivatives, quinoxaline derivatives, phenanthroline derivatives, organic aluminum complexes, and the like.

As a constituent material of the anode, a material having as a large work function as possible can be used. Examples of such a material include elemental metals such as gold, platinum, silver, copper, nickel, palladium, cobalt, selenium, vanadium, tungsten, and the like; alloys each composed of a combination of two or more of these elemental metals; and metal oxides such as tin oxide, zinc oxide, indium oxide, indium tin oxide, (ITO), indium zinc oxide, and the like. Also, conductive polymers such as polyaniline, polypyrrole, polythiophene, and the like may be used. These electrode materials may be used alone or in combination of two or more. Further, the anode may include a single layer or multiple layers.

On the other hand, as a constituent material of the cathode, a material having a small work function can be used. Examples of such a material include alkali metals such as lithium and the like; alkaline-earth metals such as calcium and the like; and elemental metals such as aluminum, titanium, manganese, silver, lead, chromium, and the like. Also, alloys each including a combination of two or more of these elemental metals can be used. Examples of the alloys include magnesium-silver, aluminum-lithium, aluminum-magnesium, and the like. Metal oxides such as indium tin oxide (ITO) can also be used. These electrode materials may be used alone or in combination of two or more. Further, the cathode may include a single layer or multiple layers.

In the organic light-emitting device according to the embodiment, the layer containing the organic compound according to the present invention and layers containing other organic compounds are formed by a method described below. In general, a thin film is formed by a vacuum deposition method, an ionic vapor deposition method, sputtering, plasma, or a known application method using a solution in a proper solvent (for example, spin coating, dipping, a casting method, a LB method, or an ink jet method). A layer formed by the vacuum deposition or solution application method causes little crystallization and has excellent time stability. In addition, the application method can form a film in combination with an appropriate binder resin.

Examples of the binder resin include, but are not limited to, polyvinylcarbazole resins, polycarbonate resins, polyester resins, ABS resins, acrylic resins, polyimide resins, phenol resins, epoxy resins, silicone resins, urea resins, and the like. These binder resins may be used alone as a homopolymer or a copolymer or used as a mixture of two or more. Further, if required, additives such as a known plasticizer, antioxidant, ultraviolet absorber, and the like may be combined.

The organic light-emitting device according to the embodiment can be used as a component member of a display device or an illuminating device. Other applications include an exposure light source of an electrophotographic image forming apparatus, a back light of a liquid crystal display device, and the like.

The above-described display device includes the organic light-emitting device of the present invention in a display portion. The display portion includes a plurality of pixels. Each of the pixels includes the organic light-emitting device of the present invention and a TFT as an example of switching devices for controlling luminance, the anode or cathode of the organic light-emitting device being electrically connected to a drain electrode or source electrode of the TFT. In this case, the display device can be used as an image display device for PC (Personal Computer).

The display device may be an image input device including an input portion to which image information is input from area CCD (Charge-Coupled Device), linear CCD, a memory card, or the like, so that the input image is output to the display portion. In addition, the display device may be used both as a display portion which is provided in an imaging apparatus or an ink jet printer and which has the image output function of displaying the image information input from the outside and as an operational panel having the input function of inputting processing information for the image. Further, the display device may be used in a display portion of a multifunction printer.

Next, a display device using the organic light-emitting device according to the embodiment of the present invention is described with referent to FIG. 1.

FIG. 1 is a schematic sectional view showing an example of a display device including the organic light-emitting device according to the embodiment of the present invention and a TFT as an example of a switching device electrically connected to the organic light-emitting device. In a display device 20 shown in FIG. 1, two pairs of the organic light-emitting devices and the TFTs are shown in the FIGURE. The structure is described in detail below.

The display device 20 shown in FIG. 1 is provided with a substrate 1 of glass or the like and a moisture-proofing film 2 provided on the substrate 1 in order to protect the TFT or the organic compound layers. In addition, reference numeral 3 denotes a metal gate electrode, reference numeral 4 denotes a gate insulating film, and reference numeral 5 denotes a semiconductor layer.

A TFT 8 includes the semiconductor layer 5, a drain electrode 6, and a source electrode 7. An insulating film 9 is provided on the TFT 8. An anode 11 of the organic light-emitting device is connected to the source electrode 7 through a contact hole 10. The configuration of the display device is not limited to this as long as any one of the anode and the cathode is connected to any one of the source electrode and the drain electrode of the TFT.

In the display device 20 shown in FIG. 1, an organic compound layer 12 is shown as a single layer regardless of being a single layer or a multilayer organic compound layer. In addition, a first protective layer 14 and a second protective layer 15 are provided on the cathode 13 in order to suppress deterioration of the organic light-emitting device.

In the display device of the present invention, a switching device is not particularly limited, but a single crystal silicon substrate, a MIM device, or an a-Si device may be used.

EXAMPLES

The present invention is described below with reference to examples. However, the present invention is not limited to these examples.

Example 1

Synthesis of Exemplified Compound XX-1

[Chem. 12]

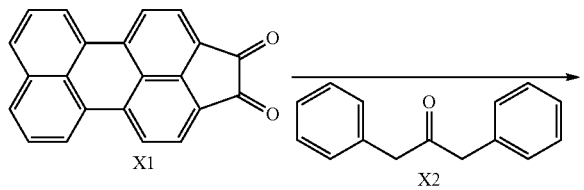

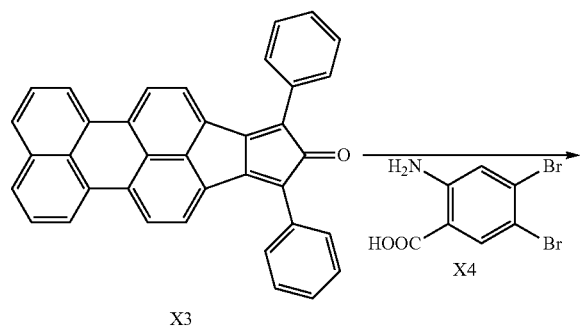

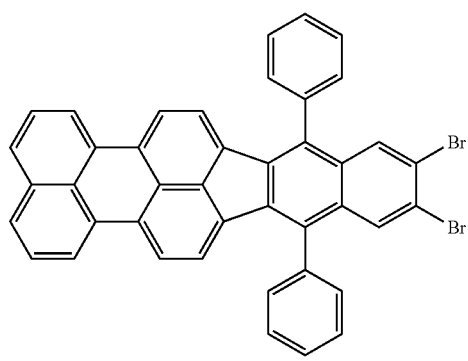

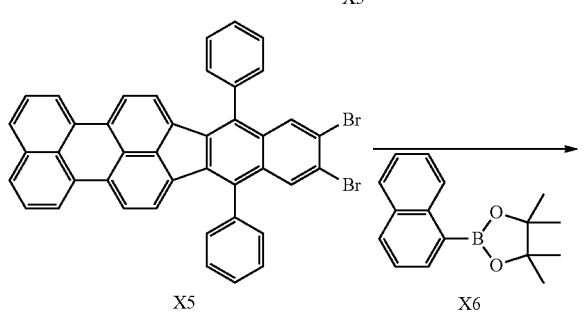

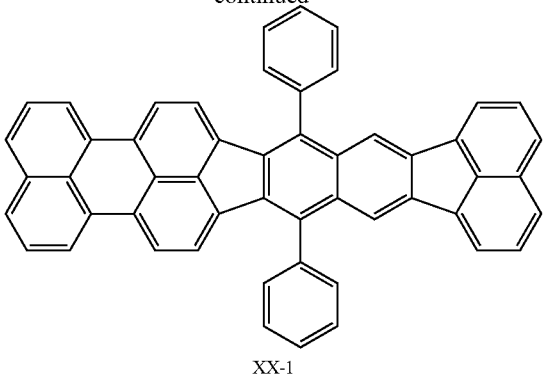

XX-1

(1) Synthesis of Compound X3

Reagents and a solvent described below were placed in a reactor.
Compound X1: 4.0 g (13 mmol)
Compound X2: 2.8 g (13 mmol)
Ethanol: 65 ml Next, the reaction solution was heated to 60° C., and then 10 ml of a 6M aqueous sodium hydroxide solution was added dropwise to the solution. After the completion of addition, the reaction solution was heated to 80° C. and stirred at this temperature (80° C.) for 2 hours. Next, the reaction solution was cooled to produce precipitates which were then filtered off. Next, the resultant precipitates were washed in order with water and ethanol and then dried by heating at 80° C. under reduced pressure to produce 6 g of compound X3 as a dark green solid (yield: 89%).

(2) Synthesis of Compound X5

Reagents and a solvent described below were placed in a reactor.
Compound X3: 5.0 g (10 mmol)
Compound X4: 6.1 g (21 mmol)
Xylene: 100 ml Next, the reaction solution was heated to 120° C., and then 6 g (21 mmol) of isoamyl nitrite was slowly added dropwise to the solution. Next, the reaction solution was heated to 140° C. and stirred at this temperature (140° C.) for 3 hours. Next, the reaction solution was cooled and then concentrated under reduced pressure to produce a brownish-red liquid. The resultant liquid was purified by column chromatography (developing solvent; toluene:heptane=2:3) and then recrystallized with chloroform/methanol to produce 4.6 g of compound X5 as yellow crystals (yield: 65%).

(3) Synthesis of Exemplified Compound XX-1

Reagents and a solvent described below were placed in a reactor.
Compound X5: 1.0 g (1.5 mmol)
Compound X6: 0.55 g (2.2 mmol)
DMF: 20 ml
Bis(dibenzylideneacetone) palladium(0): 0.84 g (1.5 mmol)
1,8-Diazabicyclo[5.4.0]undec-7-ene: 0.44 g (2.9 mmol)
Tricyclohexylphosphine: 0.81 g (2.9 mmol)

Next, the reaction solution was heated to 150° C. and stirred at this temperature (150° C.) for 4 hours. Next, the reaction solution was cooled and then concentrated under reduced pressure to produce a dark-red solid. The resultant solid was purified by column chromatography (developing solvent; toluene:heptane=1:3) and then recrystallized with chloroform/methanol to produce 247 mg of dark-red exemplified compound XX-1 (yield: 26%).

As a result of measurement of the purity of the resultant compound with HPLC (High-Performance Liquid Chromatography), the purity was confirmed to be 99% or more.

In addition, an emission spectrum of a toluene solution ($1\times10^{-5}$ mol/L) of exemplified compound XX-1 was measured. Specifically, photoluminescence was measured at an excitation wavelength of 350 nm using Hitachi F-4500. As a result, an emission spectrum having a peak intensity at 550 nm was obtained.

In addition, the compound was identified by measuring the molecular weight using JMS-T100TD (DART-TOF-MASS) manufactured by JEOL, Ltd.

DART-TOF-MASS: M+H=563.2

Example 2

Synthesis of Exemplified Compound XX-2

[Chem. 13]

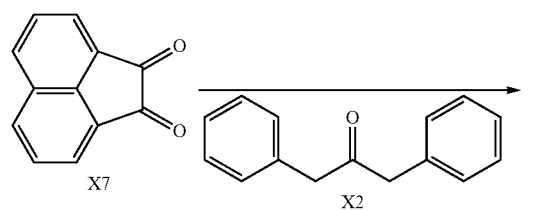

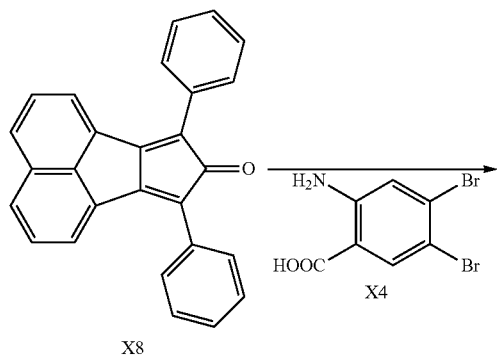

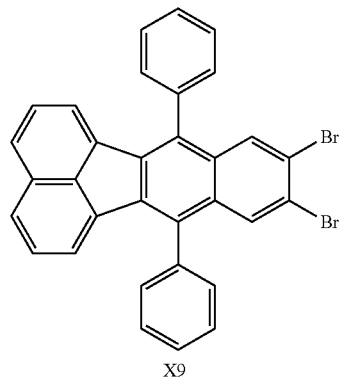

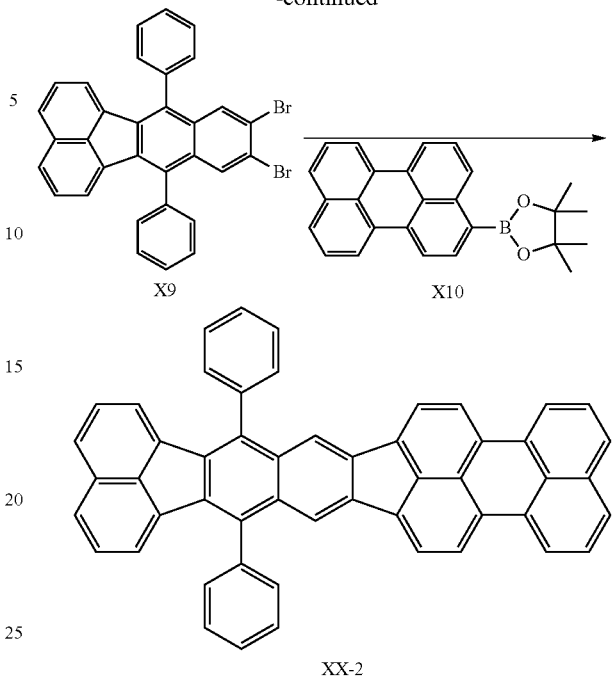

(1) Synthesis of Compound X8

Reagents and a solvent described below were placed in a reactor.

Compound X7: 10 g (55 mmol)

Compound X2: 12 g (55 mmol)

Ethanol: 200 ml

Next, the reaction solution was heated to 60° C., and then 20 ml of a 6M aqueous sodium hydroxide solution was added dropwise to the solution. After the completion of addition, the reaction solution was heated to 80° C. and stirred at this temperature (80° C.) for 2 hours. Next, the reaction solution was cooled to produce precipitates which were then filtered off. Next, the resultant precipitates were washed in order with water and ethanol and then dried by heating at 80° C. under reduced pressure to produce 18 g of compound X8 as a dark green solid (yield: 92%).

(2) Synthesis of Compound X9

Reagents and a solvent described below were placed in a reactor.

Compound X8: 10 g (28 mmol)

Compound X4: 17 g (56 mmol)

Xylene: 100 ml

Next, the reaction solution was heated to 120° C., and then 6.6 g (56 mmol) of isoamyl nitrite was slowly added dropwise to the solution. Next, the reaction solution was heated to 140° C. and stirred at this temperature (140° C.) for 3 hours. Next, the reaction solution was cooled and then concentrated under reduced pressure to produce a brownish-red liquid. The resultant liquid was purified by column chromatography (developing solvent; toluene:heptane=2:3) and then recrystallized with chloroform/methanol to produce 9.6 g of compound X9 as yellow crystals (yield: 61%).

(3) Synthesis of Exemplified Compound XX-2

Reagents and a solvent described below were placed in a reactor.

Compound X9: 2.0 g (3.6 mmol)

Compound X10: 2.0 g (5.3 mmol)

DMF: 40 ml

Bis(dibenzylideneacetone) palladium(0): 2.0 g (3.6 mmol)

1,8-Diazabicyclo[5.4.0]undec-7-ene: 1.1 g (7.1 mmol)

Tricyclohexylphosphine: 2.0 g (7.1 mmol)

Next, the reaction solution was heated to 150° C. and stirred at this temperature (150° C.) for 4 hours. Next, the reaction solution was cooled and then concentrated under reduced pressure to produce a dark-red solid. The resultant solid was purified by column chromatography (developing solvent; toluene:heptane=1:3) and then recrystallized with chloroform/methanol to produce 580 mg of dark-red exemplified compound XX-2 (yield: 25%).

As a result of measurement of the purity of the resultant compound with HPLC, the purity was confirmed to be 99% or more.

In addition, an emission spectrum of a toluene solution ($1 \times 10^{-5}$ mol/L) of exemplified compound XX-2 was measured by the same method as in Example 1. As a result, an emission spectrum having a peak intensity at 550 nm was obtained.

In addition, the compound was identified by measuring the molecular weight using JMS-T100TD (DART-TOF-MASS) manufactured by JEOL, Ltd.

DART-TOF-MASS: M+H=563.2

Example 3

Synthesis of Exemplified Compound XX-5

Exemplified compound XX-5 was produced by synthesis according to the same method as in Example 2 except that in Example 2(1), compound X11 shown below was used in place of compound X2.

[Chem. 14]

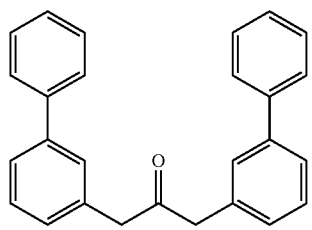

X11

As a result of measurement of the purity of the resultant compound with HPLC, the purity was confirmed to be 99.5% or more.

In addition, an emission spectrum of a toluene solution ($1 \times 10^{-5}$ mol/L) of exemplified compound XX-5 was measured by the same method as in Example 1. In this example, the excitation wavelength was 500 nm. As a result, an emission spectrum having a peak intensity at 550 nm was obtained.

In addition, the compound was identified by measuring the molecular weight using JMS-T100TD (DART-TOF-MASS) manufactured by JEOL, Ltd.

DART-TOF-MASS: M+H=805.3

Example 4

Synthesis of Exemplified Compound XX-10

Exemplified compound XX-10 was produced by synthesis according to the same method as in Example 2 except that in Example 2(1), compound X12 shown below was used in place of compound X7.

[Chem. 15]

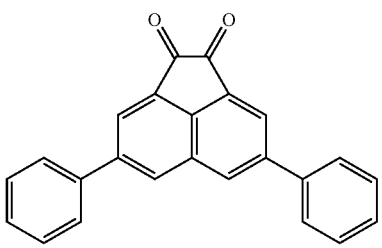

X12

As a result of measurement of the purity of the resultant compound with HPLC, the purity was confirmed to be 99.5% or more.

In addition, an emission spectrum of a toluene solution ($1 \times 10^{-5}$ mol/L) of exemplified compound XX-10 was measured by the same method as in Example 1. In this example, the excitation wavelength was 500 nm. As a result, an emission spectrum having a peak intensity at 550 nm was obtained.

In addition, the compound was identified by measuring the molecular weight using JMS-T100TD (DART-TOF-MASS) manufactured by JEOL, Ltd.

DART-TOF-MASS: M+H=805.3

Example 5

Synthesis of Exemplified Compound XY-1

Exemplified compound XY-1 was produced by synthesis according to the same method as in Example 1 except that in Example 1(3), compound X13 shown below was used in place of compound X6.

[Chem. 16]

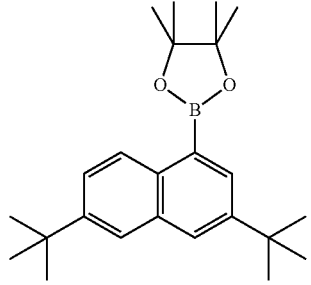

X13

As a result of measurement of the purity of the resultant compound with HPLC, the purity was confirmed to be 99.5% or more.

In addition, an emission spectrum of a toluene solution (1×10⁻⁵ mol/L) of exemplified compound XY-1 was measured by the same method as in Example 1. In this example, the excitation wavelength was 450 nm. As a result, an emission spectrum having a peak intensity at 553 nm was obtained.

In addition, the compound was identified by measuring the molecular weight using JMS-T100TD (DART-TOF-MASS) manufactured by JEOL, Ltd.

DART-TOF-MASS: M+H=765.3

Example 6

Synthesis of Exemplified Compound XY-3

Exemplified compound XY-3 was produced by synthesis according to the same method as in Example 2 except that in Example 2(1), compound X14 shown below was used in place of compound X2.

[Chem. 17]

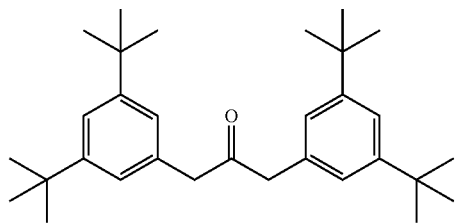

X14

As a result of measurement of the purity of the resultant compound with HPLC, the purity was confirmed to be 99.5% or more.

In addition, an emission spectrum of a toluene solution (1×10⁻⁵ mol/L) of exemplified compound XY-3 was measured by the same method as in Example 1. In this example, the excitation wavelength was 450 nm. As a result, an emission spectrum having a peak intensity at 552 nm was obtained.

In addition, the compound was identified by measuring the molecular weight using JMS-T100TD (DART-TOF-MASS) manufactured by JEOL, Ltd.

DART-TOF-MASS: M+H=877.5

Example 7

In this example, an organic light-emitting device was produced, in which an anode, a hole injection layer, a hole transport layer, a light-emitting layer, a hole-exciton blocking layer, an electron transport layer, and a cathode were sequentially formed on a substrate. Some of the materials used in the example are shown below.

[Chem. 18]

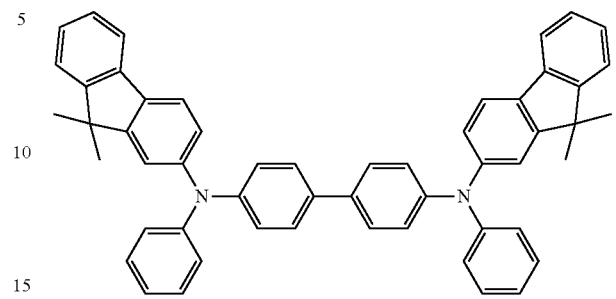

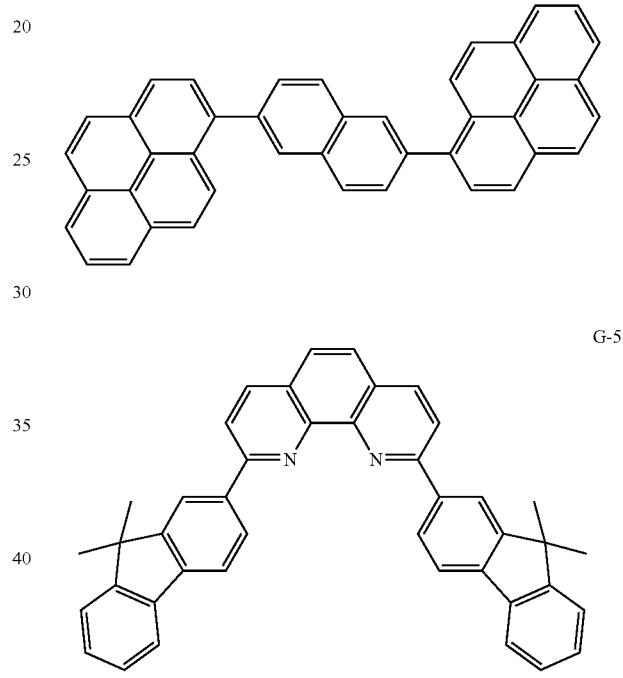

First, ITO was deposited on a glass substrate and subjected to desired patterning to form an ITO electrode (anode). In this case, the thickness of the ITO electrode was 100 nm. The substrate including the ITO electrode formed as described above was used as an ITO substrate in a subsequent step.

Next, organic compound layers and electrode layers shown in Table 4 below were continuously deposited on the ITO substrate by resistance-heating vacuum deposition in a vacuum chamber of 1×10⁻⁵ Pa. In this deposition, the electrode area of a counter electrode (a metal electrode layer, cathode) was 3 mm².

TABLE 4

| | Material | Thickness [nm] |
|---|---|---|
| Hole transport layer | G-1 | 40 |
| Light-emitting layer | G-2 (host) | 30 |
| | G-3 (assist material) | |
| | Exemplified compound | |

TABLE 4-continued

| | Material | Thickness [nm] |
|---|---|---|
| | XX-1 (guest) | |
| | (G-2:G-3:XX-1 = | |
| | 75:35:1 (weight ratio) | |
| Hole-exciton blocking layer | G-4 | 10 |
| Electron transport layer | G-5 | 30 |
| First metal electrode layer | LiF | 1 |
| Second metal electrode layer | Al | 100 |

In this example, both G-2 and G-3 are H1 shown in Table 3.

The characteristics of the resultant device were measured and evaluated. Specifically, a current-voltage characteristic was measured with microammeter 4140B manufactured by Hewlett-Packard Company, and luminance was measured with BM7 manufactured by Topcon Corporation. The results are shown in Table 5.

Examples 8 to 17

Organic light-emitting devices were produced by the same method as in Example 7 except that G-2, G-3, and the guest in Example 7 were appropriately changed to the compounds shown in Table 5. The characteristics of each of the resultant devices were measured and evaluated by the same method as in Example 7. The results of measurement are shown in Table 5. In Table 5, each of H2, H7, H10, H15, H17, H19, H21, and H23 used as G-2, and H2, H7, H10, H17, H19, H21, H23, and H24 used as G-3 was the host shown in Table 3.

TABLE 5

| | Guest | G-2 | G-3 | Luminous efficiency (cd/A) | Voltage (V) |
|---|---|---|---|---|---|
| Example 7 | XX-1 | H1 | H1 | 18 | 4.2 |
| Example 8 | XX-1 | H2 | H2 | 20 | 4.9 |
| Example 9 | XX-2 | H19 | H19 | 20 | 4.7 |
| Example 10 | XX-5 | H10 | H10 | 16 | 4.7 |
| Example 11 | XX-10 | H23 | H23 | 20 | 4.5 |
| Example 12 | XX-10 | H21 | H21 | 18 | 4.6 |
| Example 13 | XY-1 | H2 | H21 | 23 | 4.2 |
| Example 14 | XY-1 | H17 | H17 | 20 | 4.9 |
| Example 15 | XY-3 | H2 | H2 | 16 | 4.7 |
| Example 16 | XY-3 | H7 | H7 | 20 | 4.6 |
| Example 17 | XY-3 | H15 | H24 | 18 | 4.6 |

Example 18

In this example, an organic light-emitting device was produced, in which an anode, a hole injection layer, a hole transport layer, a light-emitting layer, an electron transport layer, an electron injection layer, and a cathode were sequentially formed on a substrate. The organic light-emitting device produced in this example has a resonant structure. Some of the materials used in the example are shown below.

[Chem. 19]

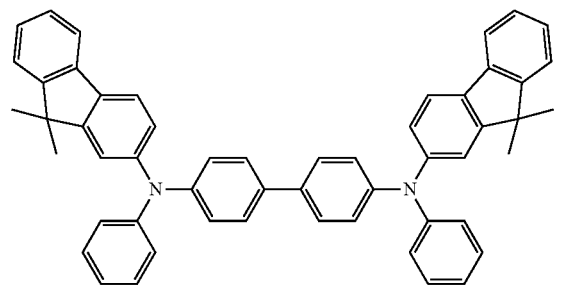

G-11

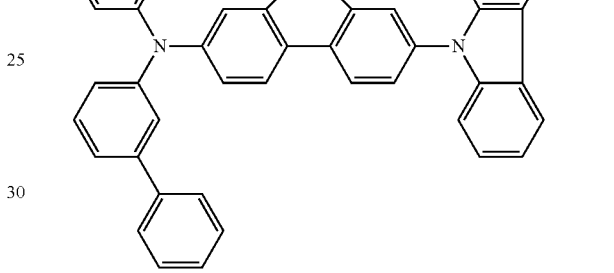

G-12

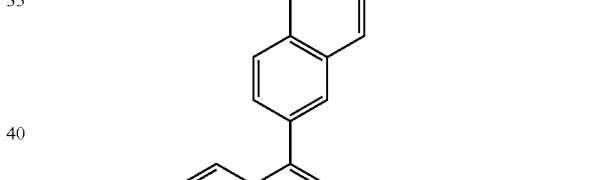

G-15

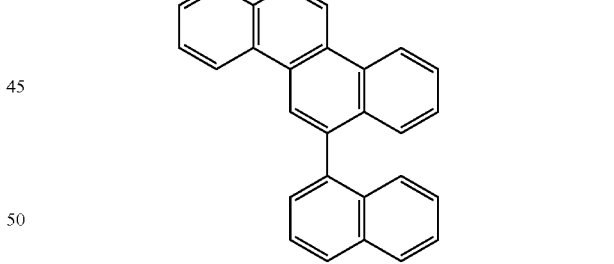

G-16

First, an aluminum alloy (AlNd) was deposited on a glass substrate (support) by sputtering to form a reflective anode. In this case, the thickness of the reflective anode was 100 nm. Next, ITO was deposited on the reflective anode by sputtering to form a transparent anode. The thickness of the transparent anode was 80 nm. Next, an acrylic element separation film was formed in a thickness of 1.5 μm around the anode and then subjected to desired patterning to provide an opening having a radius of 3 mm. Next, the substrate with the anode formed thereon was ultrasonically washed in turn with acetone and isopropyl alcohol (IPA). Next, the substrate was washed by boiling with IPA and then dried. Next, the surface of the substrate was washed with UV/ozone.

Next, the organic compound layers shown in Table 6 below were continuously deposited on the ITO substrate by resistance-heating vacuum deposition in a vacuum chamber of $1\times10^{-5}$ Pa.

TABLE 6

| | Material | Thickness [nm] |
|---|---|---|
| Hole injection layer | G-11 | 135 |
| Hole transport layer | G-12 | 10 |
| Light-emitting layer | G-13 (host) G-14 (assist material) Exemplified compound XX-1 (guest) (G-13:G-14:XX-1 = 70:29:1 (weight ratio)) | 35 |
| Electron transport layer | G-15 | 10 |
| Electron injection layer | G-16 Li (G-16:Li = 80:20 (weight ratio)) | 70 |

In this example, both G-13 and G-14 are H10 shown in Table 3.

Next, IZO was deposited on the electron injection layer by sputtering to form the cathode. The thickness of the cathode was 30 nm. Finally, sealing was performed in a nitrogen atmosphere. The organic light-emitting device was produced as described above.

The characteristics of the resultant device were measured and evaluated. Specifically, a current-voltage characteristic was measured with microammeter 4140B manufactured by Hewlett-Packard Company, and luminance was measured with BM7 manufactured by Topcon Corporation. The results are shown in Table 7.

Examples 19 and 20

Organic light-emitting devices were produced by the same method as in Example 18 except that G-13, G-14, and the guest in Example 18 were appropriately changed to the compounds shown in Table 7. The characteristics of each of the resultant devices were measured and evaluated by the same method as in Example 18. The results of measurement are shown in Table 7. In Table 7, H6 and H16 used as G-13, and H21 and H24 used as G-14 were each the host shown in Table 3.

TABLE 7

| | Guest | G-13 | G-14 | Luminous efficiency (cd/A) | Voltage (V) |
|---|---|---|---|---|---|
| Example 18 | XX-1 | H10 | H10 | 21 | 4.4 |
| Example 19 | XY-10 | H16 | H21 | 22 | 4.5 |
| Example 20 | XX-3 | H6 | H24 | 20 | 4.8 |

Example 21

In this example, an organic light-emitting device was produced, in which an anode, a hole transport layer, a first light-emitting layer, a second light-emitting layer, a hole-exciton blocking layer, an electron transport layer, and a cathode were sequentially formed on a substrate. The organic light-emitting device of this embodiment includes a plurality of light-emitting layers and thus has a mode in which the guests contained in the respective light-emitting layers individually or simultaneously emit light. Some of the materials used in the example are shown below.

[Chem. 20]

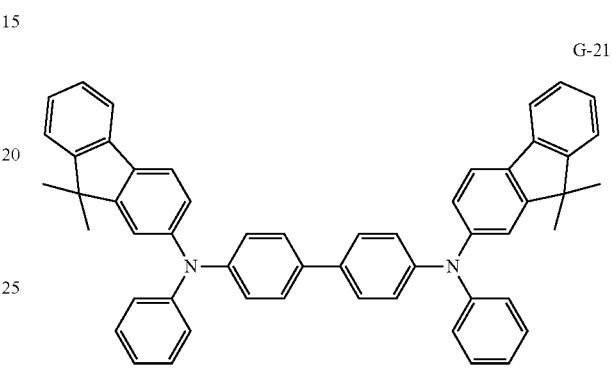

G-21

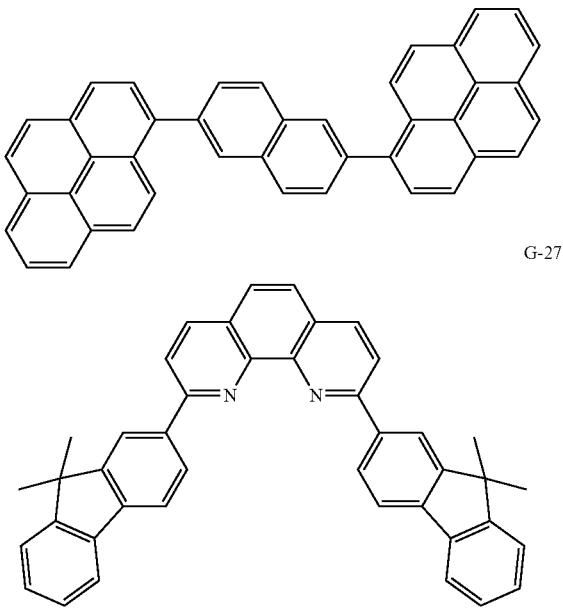

G-25

G-26

G-27

First, ITO was deposited on a glass substrate and subjected to desired patterning to form an ITO electrode. In this case, the thickness of the ITO electrode was 100 nm. The substrate with the ITO electrode formed thereon was used as an ITO substrate in a subsequent step.

Next, the organic compound layers and electrode layers shown in Table 8 below were continuously deposited on the ITO substrate by resistance-heating vacuum deposition in a vacuum chamber of $1\times10^{-5}$ Pa. The electrode area of a counter electrode (metal electrode layer, cathode) was 3 $mm^2$.

TABLE 8

| | Material | Thickness [nm] |
|---|---|---|
| Hole transport layer | G-21 | 40 |
| First light-emitting layer | G-22 (first host) G-23 (first assist material) Exemplified compound A2 (first guest) (G-22:G-23:A2 = 60:39:1 (weight ratio) | 30 |
| Second light-emitting layer | G-24 (second host) G-25 (second guest) (G-24:G-25 = 98:2 (weight ratio) | 10 |
| Hole-exciton blocking layer | G-26 | 10 |
| Electron transport layer | G-27 | 30 |
| First metal electrode layer | LiF | 1 |
| Second metal electrode layer | Al | 100 |

In this example, G-22, G-23, and G-24 are H10, H23, and H18, respectively, shown in Table 3.

The characteristics of the resultant device were measured and evaluated. Specifically, a current-voltage characteristic was measured with microammeter 4140B manufactured by Hewlett-Packard Company, and luminance was measured with BM7 manufactured by Topcon Corporation. The results are shown in Table 9.

Examples 22 and 23

Organic light-emitting devices were produced by the same method as in Example 21 except that G-22, G-23, G-24, and the guest in Example 21 were appropriately changed to the compounds shown in Table 9. The characteristics of each of the resultant devices were measured and evaluated by the same method as in Example 21. The results of measurement are shown in Table 9. In Table 9, each of H18 and H23 used as G-22, H18 and H23 used as G-23, and H4 and H10 used as G-24 was the host shown in Table 3.

TABLE 9

| | Guest | G-22 | G-23 | G-24 | Luminous efficiency (cd/A) | Voltage (V) |
|---|---|---|---|---|---|---|
| Example 21 | XX-2 | H10 | H23 | H8 | 10 | 5.6 |
| Example 22 | XY-5 | H18 | H23 | H10 | 12 | 5.4 |
| Example 23 | XX-3 | H23 | H18 | H4 | 11 | 5.3 |

As described above, the organic compound according to the present invention is a compound having a high quantum yield and light emission suitable for yellow. Therefore, when the organic compound according to the present invention is used as a constituent material of an organic light-emitting device, a light-emitting element having good emission characteristics can be produced.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-002263, filed Jan. 7, 2011, which is hereby incorporated by reference herein in its entirety.

REFERENCE SIGNS LIST

8: TFT, 11: anode, 12: organic compound layer, 13: cathode

The invention claimed is:

1. An organic compound represented by the following general formula (1);

(1)

wherein in the formula (1), $R_1$ to $R_{20}$ are each independently a hydrogen atom or a substituent selected from, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

2. The organic compound according to claim 1, wherein $R_1$ to $R_{20}$ are each independently selected from a hydrogen atom and a substituted or unsubstituted aryl group.

3. The organic compound according to claim 1, wherein $R_2$ and $R_9$ are each a substituted or unsubstituted aryl group.

4. The organic compound according to claim 1, wherein the organic compound contains two or more tert-butyl groups as substituents.

5. An organic light-emitting device comprising:
an anode and a cathode; and
at least one organic compound layer disposed between the anode and the cathode,
wherein at least one of the at least one organic compound layer contains the organic compound according to claim 1.

6. The organic light-emitting device according to claim 5, wherein the organic compound is contained in a light-emitting layer.

7. The organic light-emitting device according to claim 5, wherein yellow light is emitted.

8. A display device comprising:
a plurality of pixels,
wherein each of the plurality of pixels includes the organic light-emitting device according to claim 5 and a TFT electrically connected to the organic light-emitting device.

9. An image input device comprising:
an input portion arranged to input image information; and
a display portion arranged to output an image,
wherein the display portion has a plurality of pixels, and each of the plurality of pixels includes the organic light-emitting device according to claim 5 and a TFT electrically connected to the organic light-emitting device.

10. An illuminating device comprising the organic light-emitting device according to claim 5.

11. An exposure light source of an electrophotographic image forming apparatus comprising the organic light-emitting device according to claim 5.

12. A device comprising
an anode and a cathode; and
    at least one organic compound layer disposed between the anode and the cathode,
    wherein at least one of the at least one organic compound layer contains the organic compound according to claim 1.

* * * * *